(12) United States Patent
Aramini et al.

(10) Patent No.: US 10,196,368 B2
(45) Date of Patent: Feb. 5, 2019

(54) 2-ARYL-4-HYDROXY-1,3-THIAZOLE DERIVATIVES USEFUL AS TRPM8-INHIBITORS IN TREATMENT OF NEURALGIA, PAIN, COPD AND ASTHMA

(71) Applicant: Dompé farmaceutici S.p.A., Milan (IT)

(72) Inventors: Andrea Aramini, L'Aquila (IT); Gianluca Bianchini, L'Aquila (IT); Laura Brandolini, L'Aquila (IT); Andrea Beccari, Gignano di L'Aquila (IT); Samuele Lillini, Chiaravalle (IT); Giuseppe Nano, Scoppito (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 0 days.

(21) Appl. No.: 15/321,364

(22) PCT Filed: Jun. 23, 2015

(86) PCT No.: PCT/EP2015/064146
§ 371 (c)(1),
(2) Date: Dec. 22, 2016

(87) PCT Pub. No.: WO2015/197640
PCT Pub. Date: Dec. 30, 2015

(65) Prior Publication Data
US 2017/0190678 A1    Jul. 6, 2017

(30) Foreign Application Priority Data

Jun. 23, 2014   (EP) .................................... 14173502

(51) Int. Cl.
*C07D 277/34*   (2006.01)
*C07D 417/04*   (2006.01)
*C07D 263/42*   (2006.01)

(52) U.S. Cl.
CPC ......... *C07D 277/34* (2013.01); *C07D 263/42* (2013.01); *C07D 417/04* (2013.01)

(58) Field of Classification Search
None
See application file for complete search history.

(56) References Cited

FOREIGN PATENT DOCUMENTS

| EP | 0513379 | 11/1992 |
|---|---|---|
| EP | 2606888 | 6/2013 |
| WO | WO2006040136 | 4/2006 |
| WO | WO2007017092 | 2/2007 |
| WO | WO2007017093 | 2/2007 |
| WO | WO2007017094 | 2/2007 |
| WO | WO2007080109 | 7/2007 |
| WO | WO2007134107 | 11/2007 |
| WO | WO2009012430 | 1/2009 |
| WO | WO2010103381 | 9/2010 |
| WO | WO2010125831 | 11/2010 |
| WO | WO2013092711 | 6/2013 |

OTHER PUBLICATIONS

Beccari et al., Novel selective, potent naphthyl TRPM8 antagonists identified through a combined ligand- and structure-based virtual screening approach. Scientific Report, 2017, 7, 1-15.*
Weyer et al., Development of TRPM8 Antagonists to Treat Chronic Pain and Migraine. Pharmaceuticals, 2017, 10, 1-9.*
Reichelt et al., Synthesis and structure-activity relationship of trisubstituted thiazoles as Cdc7 kinase inhibitors. European Journal of Medicinal Chemistry, 2014, 80, 364-382.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Arcadi, Antonio, et al., "2-substituted 5-acetyl-4-thiazolyl triflates as useful building blocks for the preparation of functionalized thiazoles", Eur. J. Org. Chem. 1999, pp. 3117-3126.
Arcadi, Antonio, et al., "Pyrido[3,4-c]thiazoles through combined palladium-catalysed coupling of 2-substituted-5-acetyl-4-thiazolyitriflates with alkynes/annulation reactions", Chemistry Letters, 1999, pp. 59-60.
Bennett, Gary, J., et al., "A peripheral mononeuropathy in rat that produces disorders of pain sensation like those seen in man", Pain, 33, 1988, pp. 87-107.
Brierley, Stuart, M., et al., "A selective role for TRPV4 ion channels in visceral sensory pathways", Gastroenterology, 134(7), Jun. 2008, pp. 2059-2069.
De Groat, William, C., "A neurologic basis for the overactive bladder", Urology, 50 (Supplement 6A), Dec. 1997, pp. 37-52.
De Petrocellis, Luciano, et al., "Regulation of transient receptor potential channels of melastatin type 8 (TRPM8): Effect of cAMP, cannabinoid CB1 receptors and endovanilloids", Experimental Cell Research, 913, 2007. pp. 1911-1920.
Everaerts, Wouter, et al., "On the origin of bladder sensing: Ti(i)ps in urology", Neurology and Urodynamics. 27, 2008, pp. 264-273.

(Continued)

*Primary Examiner* — Po-Chih Chen
(74) *Attorney, Agent, or Firm* — Hueschen and Sage

(57) ABSTRACT

The invention relates to compounds acting as selective antagonists of Transient Receptor Potential cation channel subfamily M member 8 (TRPM8), and having formula (I).

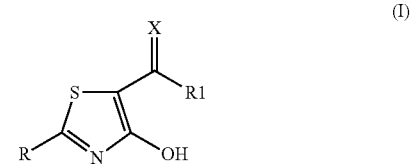

Figure 2:
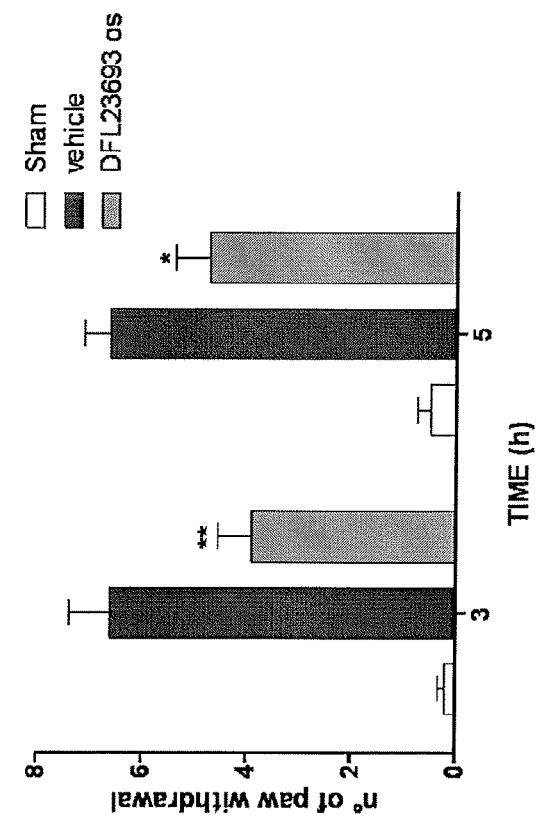
Figure 2:
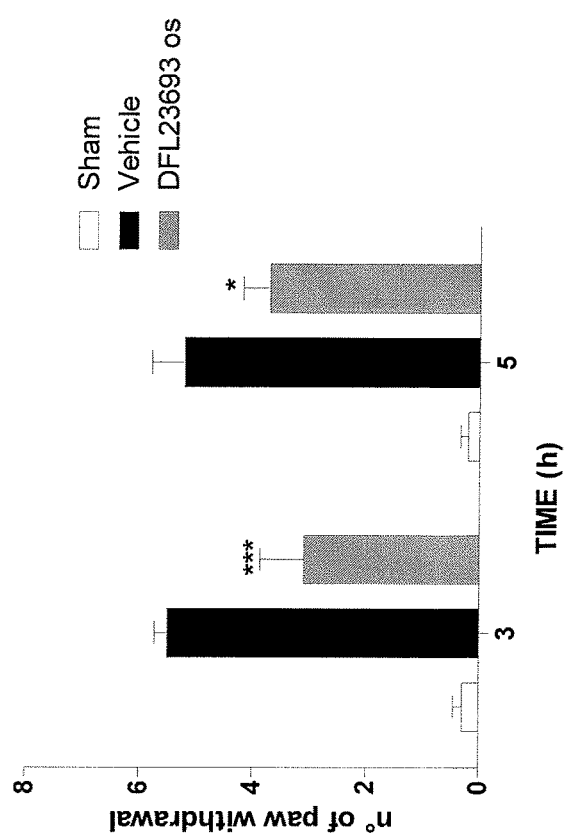

Said compounds are useful in the treatment of diseases associated with activity of TRPM8 such as pain, inflammation, ischaemia, neurodegeneration, stroke, psychiatric disorders, itch, irritable bowel diseases, cold induced and/or exacerbated respiratory disorders and urological disorders.

18 Claims, 2 Drawing Sheets

(56) References Cited

OTHER PUBLICATIONS

Giorgi, Gianluca, et al., "Mass spectrometric studies of 2-aryl-5-acetylthiazole derivatives", Journal of Mass Spectrometry, 37, 2002, pp. 169-178.
International Search Report for PCT/EP2015/064146 dated Sep. 4, 2015.
Kerdesky, Francis, A.J., et al., "4-hydrozythiazole inhibitors of 5-lipoxygenase", J. Med. Chem., 34, 1991, pp. 2158-2165.
Lazzeri, Massimo, et al., "TRP family proteins in the lower urinary tract: translating basic science into new clinical prospective", Ther Adv Urol, 1(1), 2009, pp. 33-42.
McKemy, David, D., et al., "Identification of a cold receptor reveals a general role for TRP Channels in thermosensation", Nature, vol. 416, Mar. 7, 2002, pp. 52-58.
Mukerji, Gaurav, et al., "Pain during ice water test distinguishes clinical bladder hypersensitivity from overactivity disorders", BMC Urology, 6:31, 2006.
Nilius, Bernd. "TRP channels in disease", Biochimica et Biophysica Acta, 1772, 2007, pp. 805-812.
Nilius, Bernd, et al., "Gating of TRP channels: a voltage connection?", J Physiol 567.1 2005, pp. 35-44.
Nilius, Bernd, et al., "Transient receptor potential cation channels in disease", Physiol Rev, 87, 2007, pp. 165-217.
Nilius, Bernd, et al., "TRP channels in disease", Sci. STKE 295, Aug. 2, 2005, pp. 1-9.
Peier, Andrea, M., et al., "A TRP channel that senses cold stimuli and menthol", Cell, vol. 108, Mar. 8, 2002, pp. 705-715.
Proudfoot, Clare, J., et al., "Analgesia mediated by the TRPM8 cold receptor in chronic neuropathic pain", Current Biology, 16, 22 Aug. 22, 2006, pp. 1591-1605.
Rohacs, Tibor, et al., "PI(4,5)P2 regulates the activation and desensitization of TRPM8 channels through the TRP domain", Nature Neuroscience, vol. 8, No. 5, May 2005, pp. 626-634.
Vanden-Abeele, Fabien, et al., "Membrane transport, structure, function, and biogenesis: Ca2+-independent phospholipase A2-dependent gating of TRPM8 by lysophospholipids", J. Biol. Chem. 281, 2006, pp. 40174-40182.
Voets, Thomas, et al., "Sensing with TRP channels", Nature Chemical Biology, vol. 1., No. 2, Jul. 2005 pp. 85-92.
Wissenbach, Ulrich, et al., "TRP channels as potential drug targets", Biology of the Cell, 96, 2004, pp. 47-54.
Xing, Hong, et al., "TRPM8 mechanism of autonomic nerve response to cold in respiratory airway", Molecular Pain, 4:22, 2008.
Jhaveri, M., et al., European Journal of Neuroscience, vol. 22, p. 361-370, 2005.
Database CAS, AN: 111:545. RN 1256809-34-3, Dec. 16, 2010.

\* cited by examiner

Fig. 1
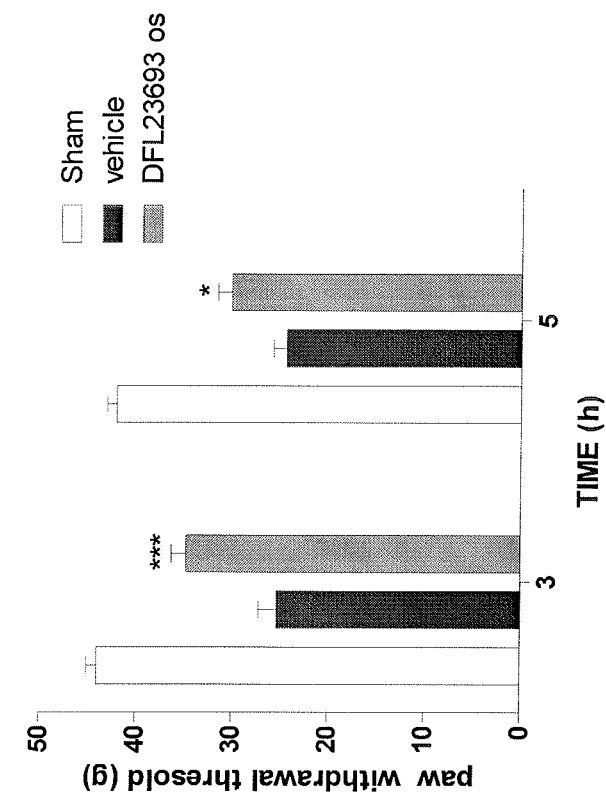
Fig. 1a
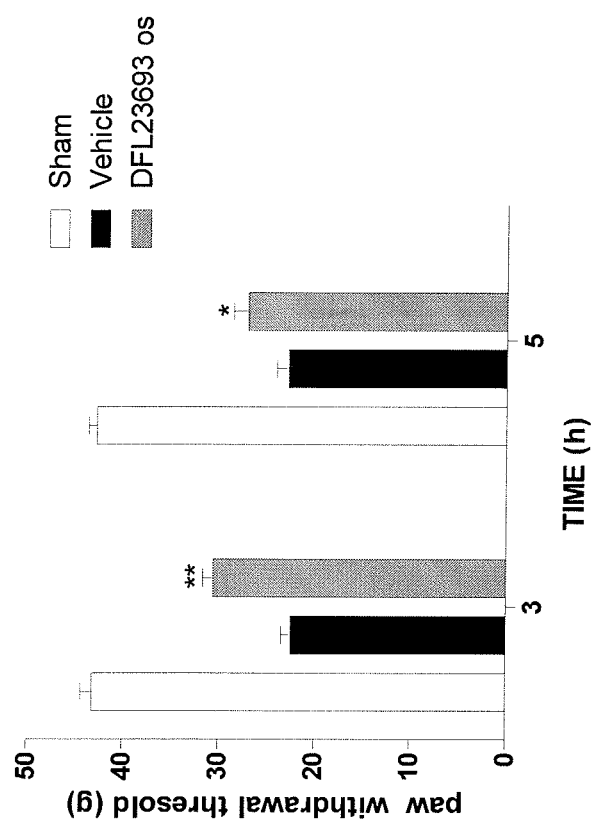
Fig. 1b

2-ARYL-4-HYDROXY-1,3-THIAZOLE DERIVATIVES USEFUL AS TRPM8-INHIBITORS IN TREATMENT OF NEURALGIA, PAIN, COPD AND ASTHMA

BRIEF DESCRIPTION OF THE INVENTION

The present invention relates to 2-aryl-4-hydroxy-1,3-thiazole derivatives that are useful for the prevention, reduction of the risk of, amelioration and/or treatment of diseases associated with the activity of the Transient Receptor Potential cation channel subfamily M member 8 (hereinafter TRPM8) also known as Cold Menthol Receptor 1 (CMR-1), and in particular for the prevention, reduction of the risk of, amelioration and/or treatment of itch, irritable bowel diseases, cold induced and/or exacerbated respiratory disorders, ischaemia, pain, neurodegeneration, psychiatric disorders, stroke and urological disorders. The invention further relates to pharmaceutical compositions containing the above compounds.

BACKGROUND OF THE INVENTION

Transient Receptor Potential (TRP) channels are one of the largest group of ion channels and, based on their sequence homology, are classified into 6 sub-families (TRPV, TRPM; TRPA, TRPC, TRPP and TRPML). TRP channels are cation-selective channels activated by several physical (such as temperature, osmolarity and mechanical stimuli) and chemical stimuli. TRPM8, which was cloned in 2002, is a non-selective cation channel of the TRP family expressed on a subpopulation of somatic sensory nerves on dorsal root ganglion and trigeminal ganglia that causes sensory nerve excitation. It is activated by mild cold temperatures and synthetic cool-mimetic compounds such as menthol, eucalyptol and icilin [McKemy D. D. et al., *Nature* (2002) 416, 52-58; Peier A. M. et al. *Cell* (2002) 108, 705-715]. Like several other TRP channels, TRPM8 is also gated by voltage [Nilius B. et al., *J. Physiol.* (2005) 567, 35-44]. The voltage dependence of TRPM8 is characterized by a strong outward rectification at depolarized transmembrane potential and a rapid and potential-dependent closure at negative membrane potentials. Cooling agents and menthol application shifts the activation curve towards more negative potentials, increasing the possibility for the opening of the channel and boosting inward currents at physiological membrane potentials. Other endogenous factors, such as phospholipase $A_2$ products [Vanden Abeele F. et al., J. Biol. Chem. (2006) 281, 40174-40182], endocannabinoids [De Petrocellis L. et al., Exp. Cell. Res. (2007) 313, 1911-1920] and PIP2 [Rohacs T. et al., Nat. Neurosci. (2005) 8, 626-634] also participate in channel regulation.

There is a lot of direct and indirect evidence of a pivotal role of TRPM8 channel activity in diseases such as pain, ischemia and itch, irritable bowel diseases, cold induced and/or exhacerbated respiratory disorders. Further, it has been demonstrated that TRP channels transduce reflex signals that are involved in the overactive bladder of patients with damaged or abnormal spinal reflex pathways [De Groat W. C. et al., Urology (1997) 50, 36-52]. TRPM8 is activated by temperatures between 8° C. and 28° C. and expressed on the primary nociceptive neurons, including bladder urothelium, dorsal root ganglia, A-delta and C-fibers. The intravesical ice water or menthol also induce C-fiber mediated spinal micturition reflex in patients with urgency and urinary incontinence [Everaerts W. et al., Neurol. Urodyn. (2008) 27, 264-73].

Furthermore, TRPM8 is known to regulate $Ca^{2+}$ concentration influxes in response to cold temperature or pharmacological stimuli. Finally, in a recent paper, the potential role of TRPM8 in cold-induced asthma and in asthma exacerbation has been proposed, suggesting TRPM8 also a relevant target for the management of these pathologies [Xing H. et al., *Molecular Pain* (2008), 4, 22-30].

The expression of the channel in brain, lung, bladder, gastrointestinal tract, blood vessels, prostate and immune cells provide further possibility for therapeutic modulation of the activity of TRPM8 in a wide range of pathologies. In particular, the disorders or diseases that have been proven to be affected by the modulation of TRPM8 are pain such as chronic pain, neuropathic pain including cold allodynia and diabetic neuropathy, postoperative pain, osteoarthritic pain, rheumatoid arthritic pain, cancer pain, neuralgia, neuropathies, algesia, fibromyalgia, nerve injury, migraine, headaches; ischaemia, neurodegeneration, stroke, psychiatric disorders, including anxiety and depression, and itch, irritable bowel diseases, cold induced and/or exhacerbated respiratory disorders such as cold induced and/or exhacerbated pulmonary hypertension, asthma and COPD; urological disorders such as painful bladder syndrome, interstitial cystitis, detrusor overactivity (overactive bladder), urinary incontinence, neurogenic detrusor overactivity (detrusor hyperflexia), idiopathic detrusor overactivity (detrusor instability), benign prostatic hyperplasia, lower urinary tract disorders and lower urinary tract symptoms [Nilius B. et al. *Science STKE* (2005), 295, re8; Voets T. et al., *Nat. Chem. Biol.* (2005), 1, 85-92; Mukerji G. et al., *Urology* (2006), 6, 31-36; Lazzeri M. et al., *Ther. Adv. Urol.* (2009), 1, 33-42; Nilius B. et al., *Biochim. Biophys. Acta* (2007), 1772, 805-12; Wissenbach U. et al., *Biol. Cell.* (2004), 96, 47-54; Nilius B. et al., *Physiol. Rev.* (2007), 87, 165-217; Proudfoot C. J. et al., *Curr. Biol.* (2006), 16, 1591-1605].

Along the last few years, several classes of non peptide TRPM8 antagonists have been disclosed. WO 2006/040136, WO 2007/017092, WO 2007/017093, WO 2007/017094, and WO 2007/080109 describe benzyloxy derivatives as TRPM8 antagonists for the treatment of urological disorders; WO 2007/134107 describes phosphorous-bearing compounds as TRPM8 antagonists for the treatment of TRPM8-related disorders; WO 2009/012430 describes sulfonamides for the treatment of diseases associated with TRPM8; WO 2010/103381 describes the use of spirocyclic piperidine derivatives as TRPM8 modulators in prevention or treatment of TRPM8-related disorders or diseases; WO 2010/125831 describes sulfamoyl benzoic acid derivatives as modulators of the TRPM8 receptor and their use in the treatment of inflammatory, pain and urological disorders; and WO 2013/092711 describes 2-aryl oxazole and thiazole derivatives as TRPM8 receptor modulators and their use in prevention, reduction of the risk of, amelioration and/or treatment of urological-related disorders.

A therapeutic area in which there is still a particularly high need for the development of antagonists of TRPM8 is that of urological disorders and associated pain. In fact, traditional drugs and medications currently available for the treatment of urinary incontinence and disorders are characterized by several side effects. For example, at the moment, the therapy of overactive bladder syndrome is based on the use of drugs, especially anticholinergic agents that affect peripheral neural control mechanisms or bladder detrusor smooth muscle contraction. These drugs inhibit parasympathetic nerves exerting a direct spasmolytic effect on the muscle of the bladder. The result of this action is the decrease of intravesicular pressure, an increase in capacity and a reduction in the frequency of bladder contraction. However, the use of anticholinergic agents is associated with serious side effects, such as dry mouth, abnormal visions, constipation and CNS disturbances, that impair the overall patient compliance. The inadequacies of the actual therapies highlight the need for novel, efficacious and safe drugs with fewer side effects.

SUMMARY OF THE INVENTION

The aim of the present invention is to provide novel antagonists of TRPM8 with high selectivity for this specific receptor and an adequate pharmacokinetic profile for use in therapy.

The present inventors have now found a class of 2-aryl-4-hydroxy-1,3-thiazole compounds acting as selective antagonists of Transient Receptor Potential cation channel subfamily M member 8 (hereinafter referred to as TRPM8), suited with good oral bioavailability and satisfying the above desiderata.

These compounds are useful in the treatment of a disease associated with the activity of TRPM8, preferably a disease deriving from overexpression and/or hyperactivity of TRPM8 receptor.

DETAILED DESCRIPTION OF THE FIGURES

FIGS. 1 and 2 show a graph with a typical response obtained in the test described in example 47.

FIG. 1 shows mechanical antiallodynic effect in rats treated with compound 2 (DFL23693os), on day 7 (FIG. 1a) and 14 (FIG. 1b) following ligation, versus sham rats (Sham) and rats that received vehicle (vehicle).

FIG. 2 shows cold antiallodynic effect in rats treated with compound 2 (DFL23693os) on day 7 (FIG. 2a) and 14 (FIG. 2b) following ligation, versus sham rats (Sham) and rats that received vehicle (vehicle).

In both Figures the sign * means $p<0.05$; sign  means $p<0.01$; sign * means $p<0.001$ vs vehicle as measured by two-way ANOVA followed by Dunnett's test.

DETAILED DESCRIPTION OF THE INVENTION

A first object of the present invention are compounds of formula (I):

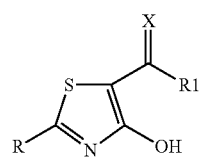

(I)

wherein
X is oxygen, sulphur, NH, NOH, or NOMe;
R is a group selected from aryl and heteroaryl, optionally substituted by one or more substituents selected from
hydrogen,
halogen,
$CF_3$,
linear or branched $C_1$-$C_6$ alkyl,
OR5 and
NR6R7, wherein R5, R6 and R7 are independently hydrogen or linear or branched $C_1$-$C_6$ alkyl;

R1 is a group selected from
linear or branched $C_1$-$C_6$ alkyl,
$(CH_2)_m$—OR2, wherein m is an integer between 1 and 3 and R2 is selected from hydrogen and linear $C_1$-$C_3$ alkyl,
$C_3$-$C_6$ cycloalkyl, and
N(R3)OR4, wherein R3 and R4 are independently hydrogen or linear or branched $C_1$-$C_3$ alkyl,
and pharmaceutically acceptable salts thereof.

According to a first preferred embodiment of the invention in said compounds of formula (I) R1 is selected from:
linear or branched $C_1$-$C_6$ alkyl,
$(CH2)_m$—OR2 wherein m is 1 and R2 is linear $C_1$-$C_3$ alkyl,
$C_3$-$C_6$ cycloalkyl, or
N(R3)OR4, wherein R3 and R4 are as defined above.

Particularly preferred compounds of the invention according to this embodiment are compounds of formula (I) wherein R1 is
linear or branched $C_1$-$C_6$ alkyl,
$(CH2)_m$—OR2 wherein m is 1 and R2 is $CH_3$,
cyclopropyl,
or
N(R3)OR4, wherein R3 and R4 are independently $C_1$-$C_3$ alkyl, preferably $CH_3$.

According to a second preferred embodiment of the invention, also in combination with the preceding embodiment, in the above compounds of formula (I), R1 is not methyl.

Particularly preferred compounds according of this embodiment are compounds wherein R1 is selected from the group consisting of ethyl, isopropyl, isobutyl, $CH_2OCH_3$, cyclopropyl and $N(CH_3)OCH_3$.

According to a third preferred embodiment of the invention, also in combination with the first embodiment, R1 is selected from the group consisting of methyl, ethyl, isopropyl, isobutyl, $CH_2OCH_3$, cyclopropyl and $N(CH_3)OCH_3$.

According to a further preferred embodiment of the invention, also in combination with the first and third embodiment, in the above compounds of formula (I) when R1 is methyl, R is not selected from 3-pyridyl, 4-chlorophenyl, 4-trifluoromethylphenyl, 3-tiophenyl, 3-thiazolyl-(2-methyl), phenyl, thiazole, 2-4-difluorophenyl, 4-methoxyiphenyl and 2-methylthiazole.

According to another preferred embodiment of the invention, also in combination with any of the preceding embodiments, X is oxygen.

According to a further preferred embodiment of the invention, also in combination with any of the preceding embodiments, said aryl is phenyl and said heteroaryl is a 5- or 6-membered heteroaryl containing from 1 to 3 heteroatoms selected from N, O and S. Preferably, said 5- or 6-membered heteroaryl is selected from the group consisting of thiophenyl, furanyl, pyrrolyl, imidazolyl, pyrazolyl, oxadiazolyl, oxazolyl and pyridinyl.

According to a further preferred embodiment of the invention, also in combination with any of the preceding embodiments, in said compounds of formula (I), wherein R is aryl, the aryl is optionally substituted with a group selected from:
halogen, preferably selected from Br and F;
linear or branched $C_1$-$C_3$ alkyl, preferably $CH_3$;
OR5 and NR6R7, wherein R5, R6 and R7 are independently hydrogen or linear $C_1$-$C_3$ alkyl.
Preferred identities of OR5 and NR6R7 are OH, $NH_2$ and $NHCH_3$, respectively.

According to a further preferred embodiment of the invention, also in combination with any of the preceding embodiments, in said compounds of formula (I), wherein R is heteroaryl, this is optionally substituted with linear or branched $C_1$-$C_6$ alkyl, preferably with $CH_3$.

Particularly preferred compounds of formula (I) of the invention are those wherein R is selected from the group consisting of 3-fluorophenyl, 4-fluorophenyl, 2-bromophenyl, 3-bromophenyl, 2-methylphenyl, 3-methylphenyl, 4-methylphenyl, 2-hydroxyphenyl, 3-hydroxyphenyl, 4-hydroxyphenyl, 3-aminophenyl, 4-aminophenyl, 3-methylaminophenyl, 4-methylaminophenyl, thiophen-2yl, furan-2yl, pyrrol-2yl, 1H-imidazol-5yl, 1-methyl-imidazol-5yl, pyrazol-4yl, 1,2,4-oxadiazol-3yl, 1,2-oxazol-5yl, pyridin-2yl, pyridin-3yl and pyridin-4yl.

Particularly preferred compounds of formula (I) according to the invention are selected from:
1-[2-(3-fluorophenyl)-4-hydroxy-1,3-thiazol-5-yl]propan-1-one (compound n. 1)
sodium 2-(3-fluorophenyl)-5-propanoyl-1,3-thiazol-4-olate (compound n. 2)
2-(3-fluorophenyl)-4-hydroxy-N-methoxy-N-methyl-1,3-thiazole-5-carboxamide (compound n. 3)
1-(2-(3-fluorophenyl)-4-hydroxythiazol-5-yl)ethanone (compound n. 4)
1-[2-(3-fluorophenyl)-4-hydroxy-1,3-thiazol-5-yl]-2-methylpropan-1-one (compound n. 5)
4-hydroxy-N-methoxy-N-methyl-2-(thiophen-2-yl)-1,3-thiazole-5-carboxamide (compound n.6)
1-[4-hydroxy-2-(thiophen-2-yl)-1,3-thiazol-5-yl]propan-1-one(compound n. 7)
4-hydroxy-N-methoxy-N-methyl-2-(2-methylphenyl)-1,3-thiazole-5-carboxamide(compound n. 8)
1-[4-hydroxy-2-(2-methylphenyl)-1,3-thiazol-5-yl]propan-1-one (compound n.9)
2-(2-bromophenyl)-4-hydroxy-N-methoxy-N-methyl-1,3-thiazole-5-carboxamide (compound n.10)
1-[4-(2-bromophenyl)-4-hydroxy-1,3-thiazol-5-yl]propan-1-one (compound n. 11)
4-hydroxy-2-(2-hydroxyphenyl)-N-methoxy-N-methyl-1,3-thiazole-5-carboxamide (compound n. 12)
1-[4-(2-hydroxyphenyl)-4-hydroxy-1,3-thiazol-5-yl]propan-1-one (compound n. 13)
1-[2-(3-bromophenyl)-4-hydroxy-1,3-thiazol-5-yl]propan-1-one (compound n. 14)
1-[4-(furan-2-yl)-4-hydroxy-1,3-thiazol-5-yl]propan-1-one (compound n. 15)
1-[4-hydroxy-2-(1H-pyrrol-2-yl)-1,3-thiazol-5-yl]propan-1-one (compound n. 16)
1-[4-hydroxy-2-(1-methyl-1H-pyrrol-2-yl)-1,3-thiazol-5-yl]propan-1-one (compound n. 17)
1-[4-hydroxy-2-(1-methyl-1H-imidazol-5-yl)-1,3-thiazol-5-yl]propan-1-one (compound n. 18)
1-[4-hydroxy-2-(1H-imidazol-5-yl)-1,3-thiazol-5-yl]propan-1-one (compound n. 19)
1-[4-hydroxy-2-(1-methyl-1H-pyrazol-4-yl)-1,3-thiazol-5-yl]propan-1-one (compound n. 20)
1-[4-hydroxy-2-(thiophen-2-yl)-1,3-thiazol-5-yl]butan-1-one (compound n. 21)
1-[4-hydroxy-2-(thiophen-2-yl)-1,3-thiazol-5-yl]-3-methylbutan-1-one (compound n. 22)
1-[4-hydroxy-2-(1,2,4-oxadiazol-3-yl)-1,3-thiazol-5-yl]propan-1-one (compound n. 23)
1-[4-hydroxy-2-(1,2-oxazol-5-yl)-1,3-thiazol-5-yl]propan-1-one (compound n. 24)
1-[4-hydroxy-2-(pyridin-3-yl)-1,3-thiazol-5-yl]propan-1-one (compound n. 25)
1-[4-hydroxy-2-(pyridin-4-yl)-1,3-thiazol-5-yl]propan-1-one (compound n. 26)
1-[4-hydroxy-2-(pyridin-2-yl)-1,3-thiazol-5-yl]propan-1-one (compound n. 27)
1-[4-hydroxy-2-(3-hydroxyphenyl)-1,3-thiazol-5-yl]propan-1-one (compound n. 28)
1-[4-hydroxy-2-(4-hydroxyphenyl)-1,3-thiazol-5-yl]propan-1-one (compound n. 29)
1-[4-hydroxy-2-(3-methylphenyl)-1,3-thiazol-5-yl]propan-1-one (compound n. 30)
1-[4-hydroxy-2-(4-methylphenyl)-1,3-thiazol-5-yl]propan-1-one (compound n. 31)
1-[2-(3-aminophenyl)-4-hydroxy-1,3-thiazol-5-yl]propan-1-one (compound n. 32)
1-[4-(4-aminophenyl)-4-hydroxy-1,3-thiazol-5-yl]propan-1-one (compound n. 33)
1-{4-hydroxy-2-[3-(methylamino)phenyl]-1,3-thiazol-5-yl}propan-1-one (compound n. 34)
1-{4-hydroxy-2-[4-(methylamino)phenyl]-1,3-thiazol-5-yl}propan-1-one (compound n. 35)
1-[4-(4-fluorophenyl)-4-hydroxy-1,3-thiazol-5-yl]propan-1-one (compound n. 36)
1-[2-(3-fluorophenyl)-4-hydroxy-1,3-thiazol-5-yl]butan-1-one (compound n. 37)
1-[2-(3-fluorophenyl)-4-hydroxy-1,3-thiazol-5-yl]-3-methylbutan-1-one (compound n. 38)
1-[2-(3-fluorophenyl)-4-hydroxy-1,3-thiazol-5-yl]-2-methoxyethanone (compound n. 39)
1-[2-(3-fluorophenyl)-4-hydroxy-1,3-thiazol-5-yl]propane-1-thione (compound n. 40)
2-(3-fluorophenyl)-4-hydroxy-N-methoxy-N-methyl-1,3-thiazole-5-carbothioamide (compound n. 41)
2-(3-fluorophenyl)-5-[(1E)-N-methoxypropanimidoyl]-1,3-thiazol-4-ol (compound n. 42)
2-(3-fluorophenyl)-5-propanimidoyl-1,3-thiazol-4-ol (compound n.43) and
2-(3-fluorophenyl)-5-[(1E)-N-hydroxypropanimidoyl]-1,3-thiazol-4-ol (compound n.44).

Most particularly preferred compounds of formula (I) according to the invention are selected from:
sodium 2-(3-fluorophenyl)-5-propanoyl-1,3-thiazol-4-olate (compound n. 2)
2-(3-fluorophenyl)-4-hydroxy-N-methoxy-N-methyl-1,3-thiazole-5-carboxamide (compound n. 3)
4-hydroxy-2-(2-hydroxyphenyl)-N-methoxy-N-methyl-1,3-thiazole-5-carboxamide (compound n. 12) and
1-[4-hydroxy-2-(3-hydroxyphenyl)-1,3-thiazol-5-yl]propan-1-one (compound n. 28).

As it will be described in details in Example 46, the present inventors have found that the above compounds 1-45 are potent antagonists of TRPM8.

In details, all of the above compounds have been tested in a high-throughput screening (HTS) cellular-based assay for the human TRPM8 and have shown an antagonist activity with a $IC_{50}$ below 2 μM.

Thus, a second object of the present invention are the above compounds of formula (I) for use as antagonists of TRPM8, preferably of human TRPM8.

Oral administration of a compound of formula (I) representative of the present invention significantly attenuated cold and mechanical allodynia at 3 hours and 5 hours post-dose. The maximal activity was reached at 3 hours after treatment (about 50% of inhibition on both the parameters), see Example 47 below.

Moreover, the same representative compound showed a high selectivity versus a wide range of selected GPCRs as well as towards TRPV1, TRPV4 and TRPA1 thus confirming its selective mechanism of action, see Example 48 below.

Finally, as reported in Example 49 below, the tested compound shows no effect towards any human cytochrome isoform thus excluding potential drug drug interaction. In addition, none effect was observed towards hERG channel thus excluding potential cardiotoxic effect during the clinical development. The low log D values of the tested compound makes it particularly suitable when ip, iv and i ves applications are required, especially in the treatment of urological disorders. At the same time, the relatively high plasma half-life and the high oral bioavailability could makes it the ideal candidate for the treatment of chronic diseases, like inflammatory and neuropathic pain.

Thus, the above disclosed compounds of the invention are particularly suitable to be used in therapy.

Accordingly, a third object of the present invention are the above compounds of formula (I) for use as medicaments.

A fourth object of the present invention are the above compounds of formula (I) for use in the prevention, reduction of the risk of, amelioration and/or treatment of a disease associated with activity of TRPM8, preferably a disease deriving from overexpression and/or hyperactivity of TRPM8 receptor.

According to the present invention, by "overexpression and/or hyperactivity of TRPM8 receptor" it is meant an expression and/or activity of TRPM8 receptor higher than at physiological level.

According to the present invention, by "disease that is associated with activity of TRPM8" it is preferably meant a disease selected from pain, itch, irritable bowel diseases, cold induced and/or exhacerbated respiratory disorders, ischaemia, neurodegeneration, stroke, urological disorders, and psychiatric disorders.

Preferably, said pain is selected from chronic pain, cancer pain, neuropathic pain, which is meant to include cold allodynia and diabetic neuropathy, postoperative pain, osteoarthritic pain, rheumatoid arthritic pain, neuralgia, neuropathies, fibromyalgia, algesia, nerve injury, migraine, headaches.

Preferably, said cold-induced and/or exhacerbated respiratory disorder is selected from cold-induced and/or exhacerbated pulmonary hypertension, COPD and asthma.

Preferably, said urological disorders are selected from painful bladder syndrome, interstitial cystitis, detrusor overactivity (also known as overactive bladder), urinary incontinence, neurogenic detrusor overactivity (also known as detrusor hyperflexia), idiopathic detrusor overactivity (also known as detrusor instability), benign prostatic hyperplasia, lower urinary tract disorders and lower urinary tract symptoms.

Preferably, said psychiatric disorders are selected from anxiety and depression.

A fifth object of the present invention are pharmaceutical compositions comprising the at least one of the above said compounds of formula (I) in combination with pharmaceutically acceptable excipients and/or diluents.

According to a preferred embodiment said pharmaceutical composition is for the prevention, reduction of the risk of, amelioration and/or treatment of a disease associated with activity of TRPM8, preferably a disease deriving from overexpression and/or hyperactivity of TRPM8 receptor.

According to a preferred embodiment, said pharmaceutical composition contains at least one of the above compounds of formula (I) as the sole active principle(s). According to an alternative preferred embodiment, said pharmaceutical composition contains at least one of the above compounds of formula (I) in association with at least one other active principle.

According to a further preferred embodiment of the invention, also in combination with the preceding embodiments, the pharmaceutical compositions may be for intravescical, intravenous, topical or oral administration.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

A sixth object of the present invention is a therapeutic method for the prevention, reduction of the risk of, amelioration and/or treatment of said disease associated with activity of TRPM8, preferably a disease deriving from overexpression and/or hyperactivity of TRPM8 receptor, comprising administering the above compound of formula (I) in a subject in need thereof.

The compounds of the invention can be administered as the sole active principles or in combination with other therapeutically active compounds.

The administration of the compounds of the invention can be effected by intravesical instillation, by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day optionally divided in multiple administrations.

The present invention shall be illustrated by means of the following examples which are not construed to be viewed as limiting the scope of the invention.

EXAMPLES

Synthesis of Preferred Compounds

The compounds listed in Table I have been synthetised following the procedures described in the following examples.

Materials and Methods

All reagents were purchased from Sigma-Aldrich, Fluorochem and Alfa Aesar and used without further purification. Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, bs=broad signal. Coupling constants (J values) are given in hertz (Hz). Analytical HPLC-MS spectra were recorded on a Thermo Finnigan Surveyor coupled with a Thermo Finnigan LCQ DECA XP-PLUS apparatus and equipped with a C18 (10 µM, 4.6 mm×150 mm) Phenomenex Gemini reverse phase column. The eluent mixture consisted of 10 mM (pH 4.2) ammonium formate/formic acid buffer and acetonitrile used according the gradient from 90:10 to 10:90 at a flow rate of 0.200 mL/min. All MS experiments were performed using electrospray ionization (ESI) in positive and negative ion mode.

All reactions were monitored by thin layer chromatography (TLC) carried out on Grace Resolv Davisil silica gel plates 250 µm thick, 60 F254, visualized by using UV (254 nm) or stains such as $KMnO_4$, p-anisaldehyde, and ceric ammonium molybdate (CAM). Chromatographic purifications were carried out on silica gel columns with Grace Resolv Davisil silica 60. All organic solutions were dried over anhydrous $Na_2SO_4$ or $MgSO_4$ and concentrated on a rotary evaporator. All compounds used for biological assays are at least of 98% purity based on HPLC analytical results monitored with 220 and 254 nm wavelengths, unless otherwise noted.

General Procedure

Example 1

Synthesis of 3-fluorobenzenecarbothioamide (Intermediate a)

A 100 mL round-bottomed flask equipped with condenser and magnetic stirrer was charged with 3-fluorobenzoamide (2.0 g, 14.4 mmol), which was dissolved in 30 mL of THF, then Lawesson's reagent was added to the solution (3.5 g, 8.64 mmol). The mixture was heated to 60° C. and stirred overnight; the transformation was monitored by TLC (Eluent: n-hexane/EtOAc 7:3). The solution was cooled at room temperature and the solvent removed by vacuum distillation.

The crude was purified by flash chromatography (Eluent: n-hexane/EtOAc 7:3) from which 3-fluorobenzenecarbothioamide was obtained as a yellow solid (2.0 g, 12.9 mmol, Y=89%).

$^1$H-NMR ($CDCl_3$): δ 7.80-7.55 (bs, 1H, N$\underline{H}_2$), 7.66-7.60 (m, 2H), 7.44-7.37 (m, 1H), 7.27-7.20 (m, 1H), 7.30-7.00 (bs, 1H, N$\underline{H}_2$).

MS ($ES^{1+}$) m/z: 156.11 $[M+H]^+$.

Synthesis of ethyl 2-(3-fluorophenyl)-4-hydroxy-1,3-thiazole-5-carboxylate (Intermediate b)

A microwave vial equipped with a magnetic stirrer was charged with 3-fluorobenzenecarbothioamide (0.5 g, 3.22 mmol) dissolved in dry ethanol (8 mL), diethylbromomalonate was added (0.055 mL, 3.22 mmol) and the vial tightly stoppered. The solution was irradiated in a microwave apparatus at 100° C. for 30 minutes. Ethyl 2-(3-fluorophenyl)-4-hydroxy-1,3-thiazole-5-carboxylate was obtained as a yellow solid after crystallization from ethanol (0.439 g, 1.64 mmol, Y=51%).

$^1$H-NMR ($CDCl_3$): δ 9.94 (bs, 1H, O$\underline{H}$), 7.80-7.70 (m, 2H), 7.49-7.41 (m, 1H), 7.2-7.17 (m, 1H), 4.43 (q, 2H, J=7.1 Hz), 1.42 (t, 3H, J=7.1 Hz).

MS ($ES^{1+}$) m/z: 267.81 $[M+H]^+$.

Synthesis of ethyl 2-(3-fluorophenyl)-4-methoxy-1,3-thiazole-5-carboxylate (Intermediate c)

A 25 mL round-bottomed flask equipped with a magnetic stirrer was charged with Ethyl 2-(3-fluorophenyl)-4-hydroxy-1,3-thiazole-5-carboxylate (0.100 g, 0.374 mmol) which was dissolved in dry THF (3 mL) and DMF (2.5 mL), the solution was treated with NaH (60-65% oil dispersion, 0.022 g, 1.5 eq) and methyl iodide (0.140 mL, 7 eq.) and stirred overnight at room temperature. The reaction was quenched in water and extracted in ethyl acetate (20 mL, 3 times), the organics were collected and washed with saturated sodium bicarbonate and brine then anhydrified over dry sodium sulphate. The crude was purified over silica gel (Eluent: n-hexane/ethyl acetate 9:1). Ethyl 2-(3-fluorophenyl)-4-methoxy-1,3-thiazole-5-carboxylate was obtained as a yellow solid (0.053 g, 0.19 mmol, Y=50%).

$^1$H-NMR ($CDCl_3$): δ 7.69-7.25 (m, 2H), 7.47-7.41 (m, 1H), 7.23-7.16 (m, 1H), 4.36 (q, 2H, J=7.2 Hz), 4.25 (s, 3H), 1.39 (t, 3H, J=7.2 Hz).

MS ($ES^{1+}$) m/z: 282.08 $[M+H]^+$.

Synthesis of 2-(3-fluorophenyl)-4-methoxy-1,3-thiazole-5-carboxylic acid (Intermediate d)

A 25 mL round-bottomed flask equipped with a magnetic stirrer was charged with Ethyl 2-(3-fluorophenyl)-4-methoxy-1,3-thiazole-5-carboxylate (0.097 g, 0.344 mmol) which was dissolved in ethanol (3 mL) and water (0.020 mL). Then KOH was added (0.193 g, 3.44 mmol) and the solution was stirred overnight at room temperature. The mixture was diluted in water (15 mL), acidified with HCl 2N to pH 2 and extracted in ethyl acetate (20 mL×2). The organic layers were collected and washed with water and brine, then anhydrified over dry sodium sulphate. 2-(3-fluorophenyl)-4-methoxy-1,3-thiazole-5-carboxylic acid was obtained as a yellow solid (0.077 g, 0.304 mmol, Y=88%).

$^1$H-NMR ($CDCl_3$): δ 7.76-7.71 (m, 2H), 7.50-7.43 (m, 1H), 7.26-7.19 (m, 1H), 4.32 (s, 3H).

MS ($ES^{1-}$) m/z: 252.25 $[M-H]^-$.

Synthesis of 2-(3-fluorophenyl)-4-methoxy-1,3-thiazole-5-carbonyl chloride (Intermediate e)

A 25 mL round-bottomed flask equipped with a magnetic stirrer and a water cooled condenser was charged with 2-(3-fluorophenyl)-4-methoxy-1,3-thiazole-5-carboxylic acid (0.049 g, 0.193 mmol) and 5 mL of dry DCM at room temperature. At the same temperature the solution was treated with an excess of thionyl chloride (0.028 mL, 0.387 mmol) and a catalytic amount of DMF (0.002 mL) then refluxed for 2.5 hours. The solution was cooled then volatiles were removed under reduced pressure. The oily residue was stripped a few times with toluene to further remove residual thionyl chloride. 2-(3-fluorophenyl)-4-methoxy-1,3-thiazole-5-carbonyl chloride as pale yellow oil was obtained (0.052 g, 0.0193 mmol, Y=95%) and used without further purification.

Synthesis of 2-(3-fluorophenyl)-N,4-dimethoxy-N-methyl-1,3-thiazole-5-carboxamide (Intermediate f)

In a 25 mL round-bottomed flask equipped with a magnetic stirrer, 2-(3-fluorophenyl)-4-methoxy-1,3-thiazole-5-carbonyl chloride (0.052 g, 0.193 mmol) was dissolved in dry DCM (5 mL) and cooled to 0° C. with an ice bath. This solution was treated with a mixture of N,O-dimethylhydroxylamine hydrochloride (0.038 g, 0.386 mmol), triethylamine (0.1 mL) and DCM (2 mL), and stirred at the same temperature for 45 minutes. As checked by LC-MS, the reaction was complete thus it was quenched and worked up as it follows: the mixture was dilute with DCM (50 mL) and washed with water (10 mL×2) and brine (10 mL) dried over anhydrous sodium sulphate and the solvent vacuum distilled. 2-(3-fluorophenyl)-N,4-dimethoxy-N-methyl-1,3-thiazole-5-carboxamide (0.060 g, 0.20 mmol, Y=95%) was obtained as an oily solid and used in the next synthetic step.

$^1$H-NMR ($CDCl_3$): δ 7.79-7.71 (m, 2H), 7.48-7.40 (m, 1H), 7.22-7.14 (m, 1H), 4.25 (s, 3H), 3.77 (s, 3H), 3.35 (s, 3H).

MS ($ES^{1+}$) m/z: 297.32 $[M+H]^+$.

Synthesis of 1-[2-(3-fluorophenyl)-4-methoxy-1,3-thiazol-5-yl]propan-1-one (Intermediate g)

A 10 mL round-bottomed flask equipped with a magnetic stirrer was charged with 2-(3-fluorophenyl)-N,4-dimethoxy-N-methyl-1,3-thiazole-5-carboxamide (0.066 g, 0.223 mmol) and 2.5 mL of dry THF was refrigerated to −78° C. The solution was treated at the same temperature ethylmagnesium chloride (0.17 mL, 0.334 mmol) then stirred at −60° C. for 1.5 hours. The cooling system was removed and the reaction quenched at room temperature with saturated aqueous ammonium chloride solution (10 mL). The mixture was extracted with ethyl acetate (20 mL×2), the organics were collected and washed twice with water (20 mL×2) and once with brine (20 mL). The organic phase was then anhydrified and the solvents vacuum removed. The crude was purified over silica gel by flash chromatography. 1-[2-(3-fluorophenyl)-4-methoxy-1,3-thiazol-5-yl]propan-1-one was obtained as a pale yellow solid (0.056 g, 0.211 mmol, Y=95%).

$^1$H-NMR (CDCl$_3$): δ 7.75-7.70 (m, 2H), 7.48-7.41 (m, 1H), 7.23-7.16 (m, 1H), 4.25 (s, 3H), 2.95 (q, 2H, J=7.3 Hz), 1.21 (t, 3H, J=7.3 Hz).

MS (ES$^{1+}$) m/z: 266.30 [M+H]$^+$.

Synthesis of 1-[2-(3-fluorophenyl)-4-hydroxy-1,3-thiazol-5-yl]propan-1-one (1)

A 10 mL round-bottomed flask equipped with a magnetic stirrer was charged with 1-[2-(3-fluorophenyl)-4-methoxy-1,3-thiazol-5-yl]propan-1-one (0.042 g, 0.158 mmol) and dissolved at room temperature in dry DCM (4 mL) then refrigerated to 0° C. with an ice bath. The solution was treated at this temperature with boron tribromide 1M in dichloromethane (0.39 mL, 0.390 mmol) then stirred for 30 minutes. The reaction was diluted with DCM (20 mL) and stirred with water (10 mL) for 10 minutes. The organic layer was separated and anhydrified over anhydrous sodium sulphate, the solvent was distilled and the crude purified over silica gel. 1-[2-(3-fluorophenyl)-4-hydroxy-1,3-thiazol-5-yl]propan-1-one was obtained as a yellow solid (0.029 g, 0.115 mmol, Y=73%)

$^1$H-NMR (CDCl$_3$): δ 11.90 (bs, 1H, OH), 7.83-7.79 (m, 1H), 7.79-7.74 (m, 1H), 7.51-7.43 (m, 1H), 7.28-7.21 (m, 1H), 2.80 (q, 2H, J=7.3 Hz), 1.30 (t, 3H, J=7.3 Hz).

MS (ES$^{1+}$) m/z: 252.12 [M+H]$^+$, MS (ES$^{1-}$) m/z: 250.11 [M-1]$^-$.

Example 2

Synthesis of sodium 2-(3-fluorophenyl)-5-propanoyl-1,3-thiazol-4-olate (2)

A 25 mL round-bottomed flask equipped with a magnetic stirrer was charged with 1-[2-(3-fluorophenyl)-4-hydroxy-1,3-thiazol-5-yl]propan-1-one (0.034 g, 0.135 mmol) and dissolved at room temperature in methanol (6 mL). The solution was then treated with an equivalent of NaOH (0.135 mL, 0.135 mmol, 1M in methanol) and stirred for 30 minutes. The volatiles were vacuum distilled and the title compound was obtained as an off-white solid in quantitative yield (0.037 g, 0.135 mmol).

$^1$H-NMR (DMSO-d$_6$): δ 7.69-7.66 (m, 1H), 7.63-7.60 (m, 1H), 7.53-7.47 (m, 1H), 7.32-7.29 (m, 1H), 2.77 (q, 2H, J=7.4 Hz), 0.97 (t, 3H, J=7.4 Hz).

MS (ES$^{1+}$) m/z: 252.25 [M+H]$^+$.

Example 3

Synthesis of 1-(2-(3-fluorophenyl)-4-hydroxythiazol-5-yl)ethanone (4)

Starting from 3-fluorobenzenecarbothioamide (0.110 g, 0.70 mmol) prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was subjected to the same synthetic conditions specified in the general procedure using methylmagnesium chloride to obtain 1-(2-(3-fluorophenyl)-4-methoxythiazol-5-yl)ethanone, which was then deprotected with boron tribromide to obtain the title compound as an off-white solid (0.030 g, 0.13 mmol, Y=87%).

$^1$H-NMR (CDCl$_3$): δ 7.85-7.71 (m, 2H), 7.55-7.40 (m, 1H), 7.30-7.19 (m, 1H), 2.50 (s, 3H).

MS (ES$^{1+}$) m/z: 238.0 [M+H]$^+$.

Example 4

Synthesis of 1-[2-(3-fluorophenyl)-4-hydroxy-1,3-thiazol-5-yl]-2-methylpropan-1-one (5)

Starting from 3-fluorobenzenecarbothioamide (0.070 g, 0.45 mmol) prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was subjected to the same synthetic conditions specified in the general procedure using isopropylmagnesium chloride to obtain 1-[2-(3-fluorophenyl)-4-methoxy-1,3-thiazol-5-yl]-2-methylpropan-1-one, which was then deprotected with boron tribromide to obtain the title compound as a yellow solid (0.021 g, 0.08 mmol, Y=88%).

$^1$H-NMR (CDCl$_3$): δ 7.85-7.71 (m, 2H), 7.55-7.40 (m, 1H), 7.30-7.19 (m, 1H), 2.50 (m, 1H), 1.30 (d, 6H, J=7.0 Hz).

MS (ES$^{1+}$) m/z: 266.0 [M+H]$^+$.

Example 5

Synthesis of 1-[4-hydroxy-2-(thiophen-2-yl)-1,3-thiazol-5-yl]propan-1-one (7)

Starting from thiophene-2-carbothioamide (0.074 g, 0.52 mmol) prepared as described in Example 1—intermediate a, the general procedure for the thiazoles synthesis was applied to obtain N,4-dimethoxy-N-methyl-2-(thiophen-2-yl)-1,3-thiazole-5-carboxamide (Weinreb's amide). The latter was subjected to the same synthetic conditions specified in the general procedure using ethylmagnesium chloride to obtain 1-[4-methoxy-2-(thiophen-2-yl)-1,3-thiazol-5-yl]propan-1-one which was then deprotected with boron tribromide to obtain the title compound as a yellow solid (0.022 g, 0.09 mmol, Y=88%).

$^1$H-NMR (CDCl$_3$): δ 7.70 (s, 1H), 7.52 (s, 1H), 7.11 (s, 1H), 2.70 (q, 2H, J=7.1 Hz), 1.28 (t, 3H, J=7.1 Hz).

MS (ES$^{1+}$) m/z: 240.1 [M+H]$^+$.

Example 6

Synthesis of 1-[4-hydroxy-2-(2-methylphenyl)-1,3-thiazol-5-yl]propan-1-one (9)

Starting from 2-methylbenzenecarbothioamide (0.152 g, 1.0 mmol) prepared analogously to what described in Example 1—intermediate a, the general procedure for the thiazoles synthesis was applied to obtain N,4-dimethoxy-N-methyl-2-(2-methylphenyl)-1,3-thiazole-5-carboxamide (Weinreb's amide). The latter was subjected to the same synthetic conditions specified in the general procedure using ethylmagnesium chloride to obtain 1-[4-methoxy-2-(2-methylphenyl)-1,3-thiazol-5-yl]propan-1-one which was then deprotected with boron tribromide to obtain the title compound as a brown solid (0.44 g, 0.18 mmol, Y=89%).

$^1$H-NMR (CDCl$_3$): δ 7.95-7.83 (m, 1H), 7.48-7.21 (m, 3H), 2.78 (q, 2H, J=7.1 Hz), 1.28 (t, 3H, J=7.1 Hz).

MS (ES$^{1+}$) m/z: 248.1 [M+H]$^+$.

Example 7

Synthesis of 1-[2-(2-bromophenyl)-4-hydroxy-1,3-thiazol-5-yl]propan-1-one (11)

Starting from 2-bromobenzenecarbothioamide (0.053 g, 0.15 mmol) prepared analogously to what described in Example 1—intermediate a, the general procedure for the thiazoles synthesis was applied to obtain 2-(2-bromophenyl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-[4-(2-bromophenyl)-4-methoxy-1,3-thiazol-5-yl]propan-1-one which was then deprotected with boron tribromide to obtain the title compound as a yellow solid (0.018 g, 0.06 mmol, Y=87%).

$^1$H-NMR (CDCl$_3$): δ 8.35-8.28 (m, 1H), 7.75-7.65 (m, 1H), 7.50-7.37 (m, 1H), 7.37-7.28 (m, 1H), 2.80 (q, 2H, J=7.0 Hz), 1.28 (t, 3H, J=7.0).

MS (ES$^{1+}$) m/z: 312.10 [M+H]$^+$.

Example 8

Synthesis of 1-[2-(2-hydroxyphenyl)-4-hydroxy-1,3-thiazol-5-yl]propan-1-one (13)

Starting from 2-methoxybenzenecarbothioamide (0.061 g, 0.35 mmol) prepared analogously to what described in Example 1—intermediate a, the general procedure was applied for the thiazoles synthesis to obtain N,4-dimethoxy-2-(2-methoxyphenyl)-N-methyl-1,3-thiazole-5-carboxamide (Weinreb's amide). The Weinreb's amide was subjected to the same synthetic conditions specified in the general procedure using ethylmagnesium chloride to obtain 1-[4-methoxy-2-(2-methoxyphenyl)-1,3-thiazol-5-yl]propan-1-one which was then deprotected with boron tribromide (4 equivalents) to obtain the title compound as a yellow solid (0.016 g, 0.07 mmol, Y=95%).

$^1$H-NMR (CDCl$_3$): δ 12.27 (s, 1H, OH), 11.55 (s, 1H, OH), 7.69-7.61 (m, 1H), 7.40-7.30 (m, 1H), 7.08-6.98 (m, 1H), 6.93-6.86 (m, 1H), 2.77 (q, 2H, J=7.0 Hz), 1.26 (t, 3H, J=7.0 Hz).

MS (ES$^{1+}$) m/z: 250.10 [M+H]$^+$.

Example 9

Synthesis of 1-[2-(3-bromophenyl)-4-hydroxy-1,3-thiazol-5-yl]propan-1-one (14)

Starting from 3-bromobenzenecarbothioamide (0.20 g, 0.92) mmol prepared analogously to what described in Example 1—intermediate a, the general procedure for the thiazoles synthesis was applied to obtain 2-(3-bromophenyl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-[2-(3-bromophenyl)-4-methoxy-1,3-thiazol-5-yl]propan-1-one which was then deprotected with boron tribromide to obtain the title compound as a white solid (0.055 g, 0.17 mmol, Y=95%).

$^1$H-NMR (CDCl$_3$): δ 11.89 (bs, 1H, OH), 8.23-8.18 (m, 1H), 7.89-7.91 (m, 1H), 7.69-7.63 (m, 1H), 7.41-7.34 (m, 1H), 2.80 (q, 2H, J=7.0 Hz), 1.30 (t, 3H, J=7.0 Hz).

MS (ES$^{1+}$) m/z: 312.1 [M+H]$^+$.

Example 10

Synthesis of 1-[2-(furan-2-yl)-4-hydroxy-1,3-thiazol-5-yl]propan-1-one (15)

Starting from furan-2-carbothioamide (0.101 g, 0.79 mmol) prepared analogously to what described in Example 1—intermediate a, the general procedure for the thiazoles synthesis was applied to obtain 2-(furan-2-yl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-[2-(furan-2-yl)-4-methoxy-1,3-thiazol-5-yl]propan-1-one which was then deprotected with boron tribromide to obtain the title compound as a yellow solid (0.034 g, 0.15 mmol, Y=90%).

$^1$H-NMR (CDCl$_3$): δ 7.60 (s, 1H), 7.15 (d, 1H, J=3.6 Hz), 6.52 (d, 1H, J=3.6 Hz), 2.95 (q, 2H, J=7.3 Hz), 1.21 (t, 3H, J=7.3 Hz).

MS (ES$^{1+}$) m/z: 224.3 [M+H]$^+$.

Example 11

Synthesis of 1-[4-hydroxy-2-(1H-pyrrol-2-yl)-1,3-thiazol-5-yl]propan-1-one (16)

Starting from 1H-pyrrole-2-carbothioamide (0.103 g, 0.82) prepared analogously to what described in Example 1—intermediate a, the general procedure for the thiazoles synthesis was applied to obtain N,4-dimethoxy-N-methyl-2-(1H-pyrrol-2-yl)-1,3-thiazole-5-carboxamide (Weinreb's amide). The latter was subjected to the same synthetic conditions specified in the general procedure using ethylmagnesium chloride to obtain 1-[4-methoxy-2-(1H-pyrrol-2-yl)-1,3-thiazol-5-yl]propan-1-one which was then deprotected with boron tribromide to obtain the title compound as a yellow solid (0.034 g, 0.15 mmol, Y=93%).

$^1$H-NMR (CDCl$_3$): δ 11.89 (bs, 1H, OH), 8.10 (vbs, 1HNH), 7.10-6.80 (m, 2H), 6.20-6.05 (m, 1H), 2.95 (q, 2H, J=7.3 Hz), 1.21 (t, 3H, J=7.3 Hz).

MS (ES1+) m/z: 223.2 [M+H]$^+$.

Example 12

Synthesis of 1-[4-hydroxy-2-(1-methyl-1H-pyrrol-2-yl)-1,3-thiazol-5-yl]propan-1-one (17)

Starting from 1-methyl-1H-pyrrole-2-carbothioamide (0.105 g, 0.75 mmol) prepared analogously to what described in Example 1—intermediate a, the general procedure for the thiazoles synthesis was applied to obtain N,4-dimethoxy-N-methyl-2-(1-methyl-1H-pyrrol-2-yl)-1,3-thiazole-5-carboxamide (Weinreb's amide). The latter was subjected to the same synthetic conditions specified in the general procedure using ethylmagnesium chloride to obtain 1-[4-methoxy-2-(1-methyl-1H-pyrrol-2-yl)-1,3-thiazol-5-yl]propan-1-one which was then deprotected with boron tribromide to obtain the title compound as a yellow solid (0.034 g, 0.14 mmol, Y=91%).

$^1$H-NMR (CDCl$_3$): δ 11.51 (bs, 1H, OH), 7.10-6.95 (m, 1H), 6.95-6.75 (m, 1H), 6.19-6.05 (m, 1H), 3.73 (s, 3H), 2.95 (q, 2H, J=7.3 Hz), 1.21 (t, 3H, J=7.3 Hz).

MS (ES$^{1+}$) m/z: 237.3 [M+H]$^+$.

Example 13

Synthesis of 1-[4-hydroxy-2-(1-methyl-1H-imidazol-5-yl)-1,3-thiazol-5-yl]propan-1-one (18)

Starting from 1-methyl-1H-imidazole-5-carbothioamide (0.203 g, 1.44 mmol) prepared analogously to what described in Example 1—intermediate a, the general procedure for the thiazoles synthesis was applied to obtain N,4-dimethoxy-N-methyl-2-(1-methyl-1H-imidazol-5-yl)-1,3-thiazole-5-carboxamide(Weinreb's amide). The latter was subjected to the same synthetic conditions specified in the general procedure using ethylmagnesium chloride to obtain 1-[4-methoxy-2-(1-methyl-1H-imidazol-5-yl)-1,3-thiazol-5-yl]propan-1-one which was then deprotected with boron tribromide to obtain the title compound as a yellow solid (0.065 g, 0.27 mmol, Y=94%).

$^1$H-NMR (CDCl$_3$): δ 11.65 (bs, 1H, OH), 7.91-7.70 (m, 1H), 7.52-7.40 (m, 1H), 3.33 (s, 3H), 2.95 (q, 2H, J=7.3 Hz), 1.21 (t, 3H, J=7.3 Hz).

MS (ES$^{1+}$) m/z: 238.4 [M+H]$^+$.

Example 14

Synthesis of 1-[4-hydroxy-2-(1H-imidazol-5-yl)-1,3-thiazol-5-yl]propan-1-one (19)

Starting from 1H-imidazole-5-carbothioamide (0.198 g, 1.56 mmol) prepared analogously to what described in Example 1—intermediate a, the general procedure for the thiazoles synthesis was applied to obtain 2-(1H-imidazol-5-yl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-[4-methoxy-2-(1H-imidazol-5-yl)-1,3-thiazol-5-yl]propan-1-one which was then deprotected with boron tribromide to obtain the title compound as a yellow solid (0.062 g, 0.28 mmol, Y=89%).

$^1$H-NMR (CDCl$_3$): δ 8.20-8.10 (m, 1H); 7.40-7.30 (m, 1H), 2.95 (q, 2H, J=7.3 Hz), 1.20 (t, 3H, J=7.3 Hz).

MS (ES$^{1+}$) m/z: 224.4 [M+H]$^+$.

Example 15

Synthesis of 1-[4-hydroxy-2-(1-methyl-1H-pyrazol-4-yl)-1,3-thiazol-5-yl]propan-1-one (20)

Starting from 1-methyl-1H-pyrazole-4-carbothioamide (0.211 g, 1.49 mmol) prepared analogously to what described in Example 1—intermediate a, the general procedure for the thiazoles synthesis was applied to obtain N,4-dimethoxy-N-methyl-2-(1-methyl-1H-pyrazol-4-yl)-1,3-thiazole-5-carboxamide (Weinreb's amide). The latter was subjected to the same synthetic conditions specified in the general procedure using ethylmagnesium chloride to obtain 1-[4-methoxy-2-(1-methyl-1H-pyrazol-4-yl)-1,3-thiazol-5-yl]propan-1-one which was then deprotected with boron tribromide to obtain the title compound as a yellow solid (0.064 g, 0.27 mmol, Y=92%).

$^1$H-NMR (CDCl$_3$): δ 11.51 (vbs, 1H, OH), 7.90-8.75 (m, 1H); 7.65-7.45 (m, 1H), 3.70 (s, 3H), 2.95 (q, 2H, J=7.3 Hz), 1.20 (t, 3H, J=7.3 Hz).

MS (ES$^{1+}$) m/z: 238.5 [M+H]$^+$.

Example 16

Synthesis of 1-[4-hydroxy-2-(thiophen-2-yl)-1,3-thiazol-5-yl]butan-1-one (21)

Starting from thiophene-2-carbothioamide (0.20 g, 1.39 mmol) prepared analogously to what described in Example 1—intermediate a, the general procedure for the thiazoles synthesis was applied to obtain N,4-dimethoxy-N-methyl-2-(thiophen-2-yl)-1,3-thiazole-5-carboxamide (Weinreb's amide). The latter was subjected to the same synthetic conditions specified in the general procedure using propylmagnesium chloride to obtain 1-[4-methoxy-2-(thiophen-2-yl)-1,3-thiazol-5-yl]butan-1-one which was then deprotected with boron tribromide to obtain the title compound as a yellow solid (0.067 g, 0.26 mmol, Y=95%).

$^1$H-NMR (CDCl$_3$): δ 11.37 (vbs, 1H, OH), 7.80-7.60 (m, 2H); 7.22-7.09 (m, 1H), 2.51 (t, 2H, J=7.5 Hz), 1.71 (m, 2H), 0.92 (t, 3H, J=7.4 Hz).

MS (ES$^{1+}$) m/z: 254.4 [M+H]$^+$.

Example 17

Synthesis of 1-[4-hydroxy-2-(thiophen-2-yl)-1,3-thiazol-5-yl]-3-methylbutan-1-one (22)

Starting from thiophene-2-carbothioamide (0.150 g, 1.04 mmol) prepared analogously to what described in Example 1—intermediate a, the general procedure for the thiazoles synthesis was applied to obtain N,4-dimethoxy-N-methyl-2-(thiophen-2-yl)-1,3-thiazole-5-carboxamide (Weinreb's amide). The latter was subjected to the same synthetic conditions specified in the general procedure using isobutylmagnesium chloride to obtain 1-[4-methoxy-2-(thiophen-2-yl)-1,3-thiazol-5-yl]-3-methylbutan-1-one which was then deprotected with boron tribromide to obtain the title compound as a yellow solid (0.053 g, 0.20 mmol, Y=95%).

$^1$H-NMR (CDCl$_3$): δ 11.45 (vbs, 1H, OH), 7.80-7.60 (m, 2H); 7.22-7.09 (m, 1H), 2.49 (d, 2H, J=7.3 Hz), 1.90-1.70 (m, 1H), 0.89 (d, 6H, J=7.2 Hz).

MS (ES$^{1+}$) m/z: 268.2 [M+H]$^+$.

Example 18

Synthesis of 1-[4-hydroxy-2-(1,2,4-oxadiazol-3-yl)-1,3-thiazol-5-yl]propan-1-one (23)

Starting from 1,2,4-oxadiazole-3-carbothioamide (0.151 g, 1.16 mmol) prepared analogously to what described in Example 1—intermediate a, the general procedure for the thiazoles synthesis was applied to obtain N,4-dimethoxy-N-methyl-2-(1,2,4-oxadiazol-3-yl)-1,3-thiazole-5-carboxamide (Weinreb's amide). The latter was subjected to the same synthetic conditions specified in the general procedure using ethylmagnesium chloride to obtain 1-[4-methoxy-2-(1,2,4-oxadiazol-3-yl)-1,3-thiazol-5-yl]propan-1-one which was then deprotected with boron tribromide to obtain the title compound as a yellow solid (0.049 g, 0.22 mmol, Y=88%).

$^1$H-NMR (CDCl$_3$): δ 11.62 (bs, 1H, OH), 8.45 (s, 1H), 2.95 (q, 2H, J=7.3 Hz), 1.20 (t, 3H, J=7.3 Hz).

MS (ES$^{1+}$) m/z: 226.1 [M+H]$^+$.

Example 19

Synthesis of 1-[4-hydroxy-2-(1,2-oxazol-5-yl)-1,3-thiazol-5-yl]propan-1-one (24)

Starting from 1,2-oxazole-5-carbothioamide (0.148 g, 1.15 mmol) prepared analogously to what described in Example 1—intermediate a, the general procedure for the thiazoles synthesis was applied to obtain N,4-dimethoxy-N-methyl-2-(1,2-oxazol-5-yl)-1,3-thiazole-5-carboxamide (Weinreb's amide). The latter was subjected to the same synthetic conditions specified in the general procedure using ethylmagnesium chloride to obtain 1-[4-methoxy-2-(1,2-oxazol-5-yl)-1,3-thiazol-5-yl]propan-1-one which was then deprotected with boron tribromide to obtain the title compound as a yellow solid (0.048 g, 0.22 mmol, Y=89%).

$^1$H-NMR (CDCl$_3$): δ 11.41 (bs, 1H, OH), 7.51 (d, 1H, J=3.1 Hz), 6.80 (d, 1H, J=3.1 Hz), 2.96 (q, 2H, J=7.3 Hz), 1.22 (t, 3H, J=7.3 Hz).

MS (ES$^{1+}$) m/z: 225.3 [M+H]$^+$.

Example 20

Synthesis of 1-[4-hydroxy-2-(pyridin-3-yl)-1,3-thiazol-5-yl]propan-1-one (25)

Starting from pyridine-3-carbothioamide (0.186 g, 1.34 mmol) prepared analogously to what described in Example 1—intermediate a, the general procedure for the thiazoles synthesis was applied to obtain N,4-dimethoxy-N-methyl-2-(pyridin-3-yl)-1,3-thiazole-5-carboxamide (Weinreb's amide). The latter was subjected to the same synthetic conditions specified in the general procedure using ethylmagnesium chloride to obtain 1-[4-methoxy-2-(pyridin-3-yl)-1,3-thiazol-5-yl]propan-1-one which was then deprotected with boron tribromide to obtain the title compound as a yellow solid (0.060 g, 0.26 mmol, Y=89%).

$^1$H-NMR (CDCl$_3$): δ 11.56 (bs, 1H, OH), 9.15-9.00 (m, 1H), 8.75-8.65 (m, 1H), 8.35-8.25 (m, 1H), 7.66-7.56 (m, 1H), 2.94 (q, 2H, J=7.3 Hz), 1.20 (t, 3H, J=7.3 Hz).

MS (ES$^{1+}$) m/z: 235.3 [M+H]$^+$.

Example 21

Synthesis of 1-[4-hydroxy-2-(pyridin-4-yl)-1,3-thiazol-5-yl]propan-1-one (26)

Starting from pyridine-4-carbothioamide (0.175 g, 1.27 mmol) prepared analogously to what described in Example 1—intermediate a, the general procedure for the thiazoles synthesis was applied to obtain N,4-dimethoxy-N-methyl-2-(pyridin-4-yl)-1,3-thiazole-5-carboxamide (Weinreb's amide). The latter was subjected to the same synthetic conditions specified in the general procedure using ethylmagnesium chloride to obtain 1-[4-methoxy-2-(pyridin-4-yl)-1,3-thiazol-5-yl]propan-1-one which was then deprotected with boron tribromide to obtain the title compound as a yellow solid (0.054 g, 0.23 mmol, Y=92%).

$^1$H-NMR (CDCl$_3$): δ 11.56 (bs, 1H, O$\underline{H}$), 9.15-9.00 (m, 2H), 8.55-8.65 (m, 2H), 2.94 (q, 2H, J=7.3 Hz), 1.20 (t, 3H, J=7.3 Hz).

MS (ES$^{1+}$) m/z: 235.3 [M+H]$^+$.

Example 22

Synthesis of 1-[4-hydroxy-2-(pyridin-2-yl)-1,3-thiazol-5-yl]propan-1-one (27)

Starting from pyridine-2-carbothioamide (0.214 g, 1.55 mmol) prepared analogously to what described in Example 1—intermediate a, the general procedure for the thiazoles synthesis was applied to obtain N,4-dimethoxy-N-methyl-2-(pyridin-2-yl)-1,3-thiazole-5-carboxamide (Weinreb's amide). The latter was subjected to the same synthetic conditions specified in the general procedure using ethylmagnesium chloride to obtain 1-[4-methoxy-2-(pyridin-2-yl)-1,3-thiazol-5-yl]propan-1-one which was then deprotected with boron tribromide to obtain the title compound as a yellow solid (0.065 g, 0.28 mmol, Y=91%).

$^1$H-NMR (CDCl$_3$): δ 11.56 (bs, 1H, O$\underline{H}$), 8.75-8.65 (m, 1H), 8.15-8.05 (m, 1H), 7.95-7.85 (m, 1H), 7.66-7.56 (m, 1H), 2.94 (q, 2H, J=7.3 Hz), 1.20 (t, 3H, J=7.3 Hz).

MS (ES$^{1+}$) m/z: 235.3 [M+H]$^+$.

Example 23

Synthesis of 1-[4-hydroxy-2-(3-hydroxyphenyl)-1,3-thiazol-5-yl]propan-1-one (28)

Starting from 3-methoxybenzenecarbothioamide (0.105 g, 0.63 mmol) prepared analogously to what described in Example 1—intermediate a, the general procedure was applied for the thiazoles synthesis to obtain N,4-dimethoxy-2-(3-methoxyphenyl)-N-methyl-1,3-thiazole-5-carboxamide (Weinreb's amide). The Weinreb's amide was subjected to the same synthetic conditions specified in the general procedure using ethylmagnesium chloride to obtain 1-[4-methoxy-2-(3-methoxyphenyl)-1,3-thiazol-5-yl]propan-1-one which was then deprotected with boron tribromide (4 equivalents) to obtain the title compound as a yellow solid (0.029 g, 0.12 mmol, Y=91%).

$^1$H-NMR (CDCl$_3$): δ 12.37 (s, 1H, O$\underline{H}$), 11.45 (s, 1H, O$\underline{H}$), 7.70-7.10 (m, 4H), 2.82 (q, 2H, J=7.3 Hz), 1.17 (t, 3H, J=7.3 Hz).

MS (ES$^{1+}$) m/z: 250.3 [M+H]$^+$.

Example 24

Synthesis of 1-[4-hydroxy-2-(4-hydroxyphenyl)-1,3-thiazol-5-yl]propan-1-one (29)

Starting from 4-methoxybenzenecarbothioamide (0206 g, 1.23 mmol) prepared analogously to what described in Example 1—intermediate a, the general procedure was applied for the thiazoles synthesis to obtain N,4-dimethoxy-2-(4-methoxyphenyl)-N-methyl-1,3-thiazole-5-carboxamide (Weinreb's amide).

The Weinreb's amide was subjected to the same synthetic conditions specified in the general procedure using ethylmagnesium chloride to obtain 1-[4-methoxy-2-(4-methoxyphenyl)-1,3-thiazol-5-yl]propan-1-one which was then deprotected with boron tribromide (4 equivalents) to obtain the title compound as a yellow solid (0.058 g, 0.23 mmol, Y=90%).

$^1$H-NMR (CDCl$_3$): δ 12.41 (s, 1H, O$\underline{H}$), 11.55 (s, 1H, O$\underline{H}$), 7.75-7.10 (m, 4H), 2.82 (q, 2H, J=7.3 Hz), 1.17 (t, 3H, J=7.3 Hz).

MS (ES$^{1+}$) m/z: 250.3 [M+H]$^+$.

Example 25

Synthesis of 1-[4-hydroxy-2-(3-methylphenyl)-1,3-thiazol-5-yl]propan-1-one (30)

Starting from 3-methylbenzenecarbothioamide (0.086 g, 0.57 mmol) prepared analogously to what described in Example 1—intermediate a, the general procedure for the thiazoles synthesis was applied to obtain N,4-dimethoxy-N-methyl-2-(3-methylphenyl)-1,3-thiazole-5-carboxamide (Weinreb's amide). The latter was subjected to the same synthetic conditions specified in the general procedure using ethylmagnesium chloride to obtain 1-[4-methoxy-2-(3-methylphenyl)-1,3-thiazol-5-yl]propan-1-one which was then deprotected with boron tribromide to obtain the title compound as a yellow solid (0.027 g, 0.10 mmol, Y=96%).

$^1$H-NMR (CDCl$_3$): δ, 11.55 (s, 1H, O$\underline{H}$), 7.70-7.47 (m, 2H), 7.45-7.10 (m, 2H), 2.80 (q, 2H, J=7.3 Hz), 2.32 (s, 3H), 1.15 (t, 3H, J=7.3 Hz).

MS (ES$^{1+}$) m/z: 248.4 [M+H]$^+$.

Example 26

Synthesis of 1-[4-hydroxy-2-(4-methylphenyl)-1,3-thiazol-5-yl]propan-1-one (31)

Starting from 4-methylbenzenecarbothioamide (0.087 g, 0.58 mmol), prepared analogously to what described in Example 1—intermediate a, the general procedure for the thiazoles synthesis was applied to obtain N,4-dimethoxy-N-methyl-2-(4-methylphenyl)-1,3-thiazole-5-carboxamide (Weinreb's amide). The latter was subjected to the same synthetic conditions specified in the general procedure using ethylmagnesium chloride to 1-[4-methoxy-2-(4-methylphenyl)-1,3-thiazol-5-yl]propan-1-one which was then deprotected with boron tribromide to obtain the title compound as a yellow solid (0.027 g, 0.10 mmol, Y=95%).

$^1$H-NMR (CDCl$_3$): δ, 11.55 (bs, 1H, O$\underline{H}$), 7.85-7.70 (m, 2H), 7.35-7.05 (m, 2H), 2.80 (q, 2H, J=7.3 Hz), 2.32 (s, 3H), 1.15 (t, 3H, J=7.3 Hz).

MS (ES$^{1+}$) m/z: 248.2 [M+H]$^+$.

Example 27

Synthesis of 1-[2-(3-aminophenyl)-4-hydroxy-1,3-thiazol-5-yl]propan-1-one (32)

Starting from 3-nitrobenzenecarbothioamide (0.235 g, 1.35 mmol) prepared analogously to what described in Example 1—intermediate a, the general procedure for the thiazoles synthesis was applied to obtain N,4-dimethoxy-N-methyl-2-(3-nitrophenyl)-1,3-thiazole-5-carboxamide (Weinreb's amide). The latter was subjected to the same synthetic conditions specified in the general procedure using ethylmagnesium chloride to obtain 1-[4-methoxy-2-(3-nitrophenyl)-1,3-thiazol-5-yl]propan-1-one.

The compound was then dissolved in methanol and mixed with 5 equivalents of stannous chloride dihydrate thus irradiated in a microwaves apparatus for 30 minutes at 100° C.

After complete reduction of the nitro group, acid base extraction and work-up, the 1-[2-(3-aminophenyl)-4-methoxy-1,3-thiazol-5-yl]propan-1-one was obtained pure. The latter was subjected to deprotection conditions with boron tribromide affording the title compound as a yellow solid (0.033 g, 0.13 mmol, last two steps Y=51%).

$^1$H-NMR (CDCl$_3$): δ, 11.72 (vbs, 1H, OH), 7.74 (bs, 1H, NH$_2$), 7.22 (bs, 1H, NH$_2$) 7.20-6.89 (m, 3H), 6.72-6.60 (m, 1H), 2.80 (q, 2H, J=7.3 Hz), 1.15 (t, 3H, J=7.3 Hz).

MS (ES$^{1+}$) m/z: 249.3 [M+H]$^+$.

Example 28

Synthesis of 1-[2-(4-aminophenyl)-4-hydroxy-1,3-thiazol-5-yl]propan-1-one (33)

Starting from 4-nitrobenzenecarbothioamide (0.234 g, 1.35 mmol) prepared analogously to what described in Example 1—intermediate a, the general procedure for the thiazoles synthesis was applied to obtain N,4-dimethoxy-N-methyl-2-(4-nitrophenyl)-1,3-thiazole-5-carboxamide
(Weinreb's amide).The latter was subjected to the same synthetic conditions specified in the general procedure using ethylmagnesium chloride to obtain 1-[4-methoxy-2-(4-nitrophenyl)-1,3-thiazol-5-yl]propan-1-one. The compound was dissolved in methanol, mixed with 5 equivalents of stannous chloride dihydratethus and irradiated in a microwaves apparatus for 30 minutes at 100° C.

After complete reduction of the nitro group, acid extraction and work-up, the 1-[4-(4-aminophenyl)-4-methoxy-1,3-thiazol-5-yl]propan-1-one was obtained pure for subsequent deprotection with boron tribromide affording the title compound as a yellow solid (0.032 g, 0.12 mmol, last two steps Y=49%).

$^1$H-NMR (CDCl$_3$): δ, 11.63 (bs, 1H, OH), 7.75-7.45 (m, 2H; bs 1H, NH$_2$), 6.89 (vbs, 1H, NH$_2$) 6.65-6.40 (m, 2H), 2.80 (q, 2H, J=7.3 Hz), 1.15 (t, 3H, J=7.3 Hz).

MS (ES$^{1+}$) m/z: 249.4 [M+H]$^+$.

Example 29

Synthesis of 1-{4-hydroxy-2-[3-(methylamino)phenyl]-1,3-thiazol-5-yl}propan-1-one (34)

Starting from 3-(bromo)benzenecarbothioamide (0.429 g, 1.98 mmol) prepared analogously to what described in Example 1—intermediate a, the general procedure for the thiazoles synthesis was applied to obtain 2-(3-bromophenyl)-N,4-dimethoxy-N-methyl-1,3-thiazole-5-carboxamide (Weinreb's amide). The latter compound was subjected to the same synthetic conditions specified in the general procedure using ethylmagnesium chloride to obtain 1-[2-(3-bromophenyl)-4-methoxy-1,3-thiazol-5-yl]propan-1-one.

The bromo aryl thiazole derivative was then dissolved in anhydrous toluene and treated with 5 equivalents of sodium tert-butoxide, 1.5 equivalents of methylamine, 0.1 equivalents of 2-(di-terbutylphosphino)biphenyl, 0.05 equivalents of tris(dibenzylidene-acetone)dipalladium(0) and sealed in a vial thus irradiated in a microwaves apparatus at 100° C. for an hour. After chromatography, 1-{4-methoxy-2-[3-(methylamino)phenyl]-1,3-thiazol-5-yl}propan-1-one was obtained and then deprotected with boron tribromide to obtain the title compound as a yellow solid (0.020 g, 0.08 mmol, last two steps Y=21%).

$^1$H-NMR (CDCl$_3$): δ, 11.60 (bs, 1H, OH), 7.25-6.90 (m, 3H), 6.75-6.65 (m, 1H), 4.35 (vbs, 1H, NH), 3.05 (s, 3H), 2.93 (q, 2H, J=7.3 Hz), 1.25 (t, 3H, J=7.3 Hz).

MS (ES$^{1+}$) m/z: 263.4 [M+H]$^+$.

Example 30

Synthesis of 1-{4-hydroxy-2-[4-(methylamino)phenyl]-1,3-thiazol-5-yl}propan-1-one (35)

Starting from 4-(bromo)benzenecarbothioamide (0.50 g, 2.32 mmol) prepared analogously to what described in Example 1—intermediate a, the general procedure for the thiazoles synthesis was applied to obtain 2-(4-bromophenyl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-[4-(4-bromophenyl)-4-methoxy-1,3-thiazol-5-yl]propan-1-one. The bromo aryl thiazole derivative was then dissolved in anhydrous toluene and treated with 5 equivalents of sodium tert-butoxide, 1.5 equivalents of methylamine, 0.1 equivalents of 2-(di-terbutylphosphino)biphenyl, 0.05 equivalents of tris(dibenzylidene-acetone)dipalladium(0) and sealed in a vial thus irradiated in a microwaves apparatus at 100° C. for an hour. After chromatography 1-{4-methoxy-2-[4-(methylamino)phenyl]-1,3-thiazol-5-yl}propan-1-one was obtained and then O-demethylated by the action of boron tribromide affording the title compound as a yellow solid (0.015 g, 0.06 mmol, last two steps Y=13%).

$^1$H-NMR (CDCl$_3$): δ, 11.60 (bs, 1H, OH), 7.72-7.43 (m, 2H;), 6.63-6.39 (m, 2H), 4.35 (vbs, 1H, NH), 3.07 (s, 3H), 2.96 (q, 2H, J=7.3 Hz), 1.23 (t, 3H, J=7.3 Hz).

MS (ES$^{1+}$) m/z: 263.4 [M+H]$^+$.

Example 31

Synthesis of 1-[2-(4-fluorophenyl)-4-hydroxy-1,3-thiazol-5-yl]propan-1-one (36)

Starting from 4-fluorobenzenecarbothioamide (0.122 g, 0.78 mmol) prepared analogously to what described in Example 1—intermediate a, the general procedure for the thiazoles synthesis was applied to obtain 2-(4-fluorophenyl)-N,4-dimethoxy-N-methyl-1,3-thiazole-5-carboxamide (Weinreb's amide). The latter was subjected to the same synthetic conditions specified in the general procedure using ethylmagnesium chloride to obtain 1-(4-fluorophenyl)-4-methoxy-1,3-thiazol-5-yl]propan-1-one which was then deprotected with boron tribromide to obtain the title compound as a yellow solid (0.037 g, 0.15 mmol, Y=91%).

$^1$H-NMR (CDCl$_3$): δ 11.85 (bs, 1H, OH), 7.95-7.80 (m, 2H), 7.29-7.09 (m, 2H), 2.80 (q, 2H, J=7.3 Hz), 1.30 (t, 3H, J=7.3 Hz).

MS (ES$^{1+}$) m/z: 252.12 [M+H]$^+$, MS (ES$^{1-}$) m/z: 250.11 [M−H]$^-$.

Example 32

Synthesis of 1-[2-(3-fluorophenyl)-4-hydroxy-1,3-thiazol-5-yl]butan-1-one (37)

Starting from 3-fluorobenzenecarbothioamide (0.124 g, 0.80 mmol) prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was subjected to the same synthetic conditions specified in the general procedure using propylmagnesium chloride to obtain 1-[2-(3-fluorophenyl)-4-methoxy-1,3-thiazol-5-yl]butan-1-one, which was then deprotected with boron tribromide to obtain the title compound as an light yellow solid (0.028 g, 0.10 mmol, Y=81%).

$^1$H-NMR (CDCl$_3$): δ 11.90 (bs, 1H, O$\underline{H}$), 7.85-7.71 (m, 2H), 7.50-7.40 (m, 1H), 7.27-7.19 (m, 1H), 2.72 (t, 2H, J=7.3 Hz), 1.83 (q, 2H, J=7.3 Hz), 1.05 (t, 3H, J=7.3 Hz).

MS (ES$^{1+}$) m/z: 266.30 [M+H]$^+$.

Example 33

Synthesis of 1-[2-(3-fluorophenyl)-4-hydroxy-1,3-thiazol-5-yl]-3-methylbutan-1-one (38)

Starting from 3-fluorobenzenecarbothioamide (0.112 g, 0.72 mmol) prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was subjected to the same synthetic conditions specified in the general procedure using isobutylmagnesium chloride to obtain 1-[2-(3-fluorophenyl)-4-methoxy-1,3-thiazol-5-yl]-3-methylbutan-1-one, which was then deprotected with boron tribromide to obtain the title compound as an yellow solid (0.033 g, 0.12 mmol, Y=73%).

$^1$H-NMR (CDCl$_3$): δ 12.10 (bs, 1H, O$\underline{H}$), 7.83-7.73 (m, 2H), 7.50-7.43 (m, 1H), 7.28-7.21 (m, 1H), 2.62 (d, 2H, J=7.3 Hz), 2.34 (m, 1H), 1.05 (d, 6H, J=7.3 Hz).

MS (ES$^{1+}$) m/z: 280.23 [M+H]$^+$.

Example 34

Synthesis of 1-[2-(3-fluorophenyl)-4-hydroxy-1,3-thiazol-5-yl]-2-methoxyethanone (39)

1-[2-(3-fluorophenyl)-4-methoxy-1,3-thiazol-5-yl]ethanone (0.200 g, 0.79 mmol), prepared as described in Example 3, was dissolved in 10 mL of dry DCM and N-bromosuccinimide (0.142 g, 0.79 mmol) was added. The resulting mixture was stirred for 3 h at room temperature. The solvent was evaporated under vacuum distillation to obtain 2-bromo-1-[2-(3-fluorophenyl)-4-methoxy-1,3-thiazol-5-yl]ethanone which was used without further purification. The compound was then dissolved in 5 mL of glacial acetic acid, sodium acetate (0.65 g, 7.9 mmol) was added and the mixture was heated at 120° C. for 2 h. The solution was diluted with 30 mL of water and washed with diethyl ether (20 mL×3). 2-[2-(3-fluorophenyl)-4-methoxy-1,3-thiazol-5-yl]-2-oxoethyl acetate was purified by flash chromatography (n-hexane:ethyl acetate 9:1 as eluent). The latter compound was dissolved in 10 mL of 1,4-dioxane and 2 mL of NaOH 2M were added. The solution was stirred at room temperature for 2 h. The solution was diluted with 10 mL of HCl 2M and the compound extracted with ethyl acetate. 1-[2-(3-fluorophenyl)-4-methoxy-1,3-thiazol-5-yl]-2-hydroxyethanone was obtained as orange oil in 65% yield. The latter compound (0.089 g, 0.33 mmol) was dissolved in 5 mL of dry DMF and 0.016 g (0.66 mmol) of NaH (60% w/w) were added at 0° C. Then 41 µL (0.66 mmol) of methyl iodide were added and the solution was stirred at room temperature for 5 h. The mixture was quenched with 10 mL of saturated NH$_4$Cl and the compound was extracted with ethyl acetate. The crude was purified by flash chromatography with n-hexane:ethyl acetate 9:1 as eluent to obtain 1-[2-(3-fluorophenyl)-4-methoxy-1,3-thiazol-5-yl]-2-methoxyethanone in quantitative yield. 1-[2-(3-fluorophenyl)-4-methoxy-1,3-thiazol-5-yl]-2-methoxyethanone was dissolved at room temperature in dry DCM (4 mL) then refrigerated to 0° C. with an ice bath. The solution was treated at this temperature with boron tribromide 1M in dichloromethane (0.66 mL, 0.66 mmol) then stirred for 30 minutes. The reaction was diluted with DCM (10 mL) and stirred with water (10 mL) for 10 minutes. The organic layer was separated and anhydrified over anhydrous sodium sulphate, the solvent was distilled and the crude purified over silica gel.

1-[2-(3-fluorophenyl)-4-hydroxy-1,3-thiazol-5-yl]-2-methoxyethanone was obtained as a yellow solid (0.019 g, 0.071 mmol, Y=43%).

1H-NMR (CDCl$_3$): δ 7.83-7.71 (m, 2H), 7.42-7.35 (m, 1H), 7.28-7.21 (m, 1H), 2.85 (s, 2H), 2.37 (s, 3H).

MS (ES1+) m/z: 268.21 [M+H]+.

Example 35

Synthesis of 1-[2-(3-fluorophenyl)-4-hydroxy-1,3-thiazol-5-yl]propane-1-thione (40)

1-[2-(3-fluorophenyl)-4-methoxy-1,3-thiazol-5-yl]propan-1-one (0.120 g, 0.45 mmol), prepared as described in Example 1—intermediate g, was dissolved in 5 mL of dry THF. Lawesson's reagent (0.273 g, 0.675 mmol) was added and the resulting mixture was heated at 130° C. in a sealed tube for 2 h. The solution was cooled at room temperature and the solvent removed by vacuum distillation. The crude was purified by flash chromatography (n-hexane:ethyl acetate 85:15 as eluent) to obtain 1-[2-(3-fluorophenyl)-4-methoxy-1,3-thiazol-5-yl]propane-1-thione as a yellow oil (0.037 mg, 0.13 mmol, Y=29%). The latter compound was deprotected with boron tribromide as described for compound 1 to obtain the title compound as a yellow solid (0.030 g, 0.11 mmol, Y=86%).

$^1$H-NMR (CDCl$_3$): δ 11.81 (bs, 1H, O$\underline{H}$), 7.81-7.76 (m, 1H), 7.71-7.64 (m, 1H), 7.61-7.53 (m, 1$\underline{H}$), 7.28-7.20 (m, 1H), 2.85 (q, 2H, J=7.3 Hz), 1.51 (t, 3H, J=7.3 Hz).

MS (ES$^{1+}$) m/z: 268.35.12 [M+H]$^+$.

Example 36

Synthesis of 2-(3-fluorophenyl)-4-hydroxy-N-methoxy-N-methyl-1,3-thiazole-5-carboxamide (3)

Starting from 3-fluorobenzenecarbothioamide (0.055 g, 0.35 mmol), prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was then directly deprotected with boron tribromide to obtain the 2-(3-fluorophenyl)-4-hydroxy-N-methoxy-N-methyl-1,3-thiazole-5-carboxamide as a pale yellow solid (0.019 g, 0.07 mmol, Y=95%).

1H-NMR (CDCl$_3$): δ 7.85-7.70 (m, 2H), 7.45-7.35 (m, 1H), 7.25-7.19 (m, 1H), 3.85 (s, 3H), 3.37 (s, 3H).

MS (ES1+) m/z: 283.9 [M+H]+.

Example 37

Synthesis of 4-hydroxy-N-methoxy-N-methyl-2-(thiophen-2-yl)-1,3-thiazole-5-carboxamide (6)

Starting from thiophene-2-carbothioamide (0.081 g, 0.57 mmol) prepared analogously to what described in Example 1—intermediate a, the general procedure for the thiazoles synthesis was applied to obtain N,4-dimethoxy-N-methyl-2-(thiophen-2-yl)-1,3-thiazole-5-carboxamide (Weinreb's amide). The latter was directly deprotected with boron tribromide to obtain the title compound as an off-white solid (0.030 g, 0.11 mmol, Y=95%).

1H-NMR (CDCl$_3$): δ 7.68 (s, 1H), 7.48 (s, 1H), 7.08 (s, 1H), 3.80 (s, 3H), 3.35 (s, 3H).

MS (ES1+) m/z: 271.1 [M+H]+.

Example 38

Synthesis of 4-hydroxy-N-methoxy-N-methyl-2-(2-methylphenyl)-1,3-thiazole-5-carboxamide (8)

Starting from 2-methylbenzenecarbothioamide (0.103 g, 0.68 mmol) prepared analogously to what described in Example 1—intermediate a, the general procedure for the thiazoles synthesis was applied to obtain N,4-dimethoxy-N-methyl-2-(2-methylphenyl)-1,3-thiazole-5-carboxamide (Weinreb's amide). The latter was directly deprotected with boron tribromide to obtain the title compound as an off-white solid (0.037 g, 0.13 mmol, Y=95%).

1H-NMR (CDCl$_3$): δ 12.10 (s, 1H, OH), 7.84-7.78 (m, 1H), 7.41-7.20 (m, 3H), 3.80 (s, 3H), 3.38 (s, 3H), 2.62 (s, 3H).

MS (ES1+) m/z: 279.9 [M+H]+.

Example 39

Synthesis of 2-(2-bromophenyl)-4-hydroxy-N-methoxy-N-methyl-1,3-thiazole-5-carboxamide (10)

Starting from 2-bromobenzenecarbothioamide (0.051 g, 0.15 mmol) prepared analogously to what described in Example 1—intermediate a, the general procedure for the thiazoles synthesis was applied to obtain 2-(2-bromophenyl)-N,4-dimethoxy-N-methyl-1,3-thiazole-5-carboxamide (Weinreb's amide). The latter was directly deprotected with boron tribromide to obtain the title compound as a white solid (0.021 g, 0.06 mmol, Y=95%).

1H-NMR (CDCl$_3$): δ 12.00 (s, 1H, OH), 8.35-8.21 (m, 1H), 7.78-7.68 (m, 1H), 7.50-7.37 (m, 1H), 7.37-7.22 (m, 1H), 3.83 (s, 3H), 3.39 (s, 3H).

MS (ES1+) m/z: 343.04 [M+H]+.

Example 40

Synthesis of 4-hydroxy-2-(2-hydroxyphenyl)-N-methoxy-N-methyl-1,3-thiazole-5-carboxamide (12)

Starting from 2-methoxybenzenecarbothioamide (0.120 g, 0.72 mmol) prepared analogously to what described in Example 1—intermediate a, the general procedure was applied for the thiazoles synthesis to obtain N,4-dimethoxy-2-(2-methoxyphenyl)-N-methyl-1,3-thiazole-5-carboxamide (Weinreb's amide).

The Weinreb's amide was directly deprotected with boron tribromide (4 equivalents) to obtain the title compound as a yellow solid (0.040 g, 0.14 mmol, Y=95%).

1H-NMR (CDCl$_3$): δ 12.29 (s, 1H, OH), 11.60 (s, 1H, OH), 7.70-7.62 (m, 1H), 7.41-7.32 (m, 1H), 7.10-7.02 (m, 1H), 6.95-6.89 (m, 1H), 3.83 (s, 3H), 3.38 (s, 3H).

MS (ES1+) m/z: 281.1 [M+H]+.

Example 41

Synthesis of 2-(3-fluorophenyl)-4-hydroxy-N-methoxy-N-methyl-1,3-thiazole-5-carbothioamide (41)

2-(3-fluorophenyl)-N,4-dimethoxy-N-methyl-1,3-thiazole-5-carboxamide (0.100 g, 0.34 mmol), preparated as described in Example 1—intermediate f, was dissolved in 5 mL of dry THF. Lawesson's reagent (0.361 g, 0.51 mmol) was added and the resulting mixture was heated at 70° C. in for 2 h. The solution was cooled at room temperature and the solvent removed by vacuum distillation. The crude was purified by flash chromatography (n-hexane:ethyl acetate 85:15 as eluent) to obtain 2-(3-fluorophenyl)-N,4-dimethoxy-N-methyl-1,3-thiazole-5-carbothioamide as a yellow oil (0.072 g, 0.23 mmol, Y=68%). The latter compound was deprotected with boron tribromide as described for compound 1 to obtain the title compound as a yellow solid (0.057 g, 0.19 mmol, Y=85%).

1H-NMR (CDCl$_3$): δ 7.83-7.69 (m, 2H), 7.44-7.35 (m, 1H), 7.26-7.20 (m, 1H), 3.95 (s, 3H), 3.45 (s, 3H).

MS (ES1+) m/z: 299.20 [M+H]+.

Example 42

Synthesis of 2-(3-fluorophenyl)-5-[(1E)-N-methoxypropanimidoyl]-1,3-thiazol-4-ol (42)

To a solution of methyl 2-chloro-3-oxopentanoate (0.200 g, 1.215 mmol) in 5 mL of ethanol, methoxyamine hydrochloride (0.152 g, 1.823 mmol) and ammonium acetate (0.149 g, 1.823 mmol) were added and the resulting mixture was stirred at room temperature for 4 h. The mixture was diluted with water (10 mL) and extracted with ethyl ether (20 mL). The organic phase was then anhydrified over dry sodium sulphate and the solvent removed by vacuum distillation. The crude was dissolved in 5 mL of ethanol and transferred into a microwave vial; then 0.093 g (0.60 mmol) of 3-fluorobenzenecarbothioamide were added. The vial was sealed and irradiated at 100° C. for 60 minutes. The solution was cooled at room temperature and the solvent removed by vacuum distillation. The crude was purified by flash chromatography (n-hexane:ethyl acetate 90:10 as eluent) to obtain 2-(3-fluorophenyl)-5-[(1E)-N-methoxypropanimidoyl]-1,3-thiazol-4-ol as a yellow solid (0.066 mg, 0.23 mmol, Y=39%).

$^1$H-NMR (CDCl$_3$): δ 10.45 (bs, 1H, OH), 7.75-7.65 (m, 2H), 7.45-7.38 (m, 1H), 7.18-7.11 (m, 1H), 4.00 (s, 3H), 2.68 (q, 2H, J=7.3 Hz), 1.22 (t, 3H, J=7.3 Hz).

MS (ES$^{1+}$) m/z: 281.12 [M+H]$^+$.

Example 43

Synthesis of 2-(3-fluorophenyl)-5-propanimidoyl-1,3-thiazol-4-ol (43)

To a solution of methyl 2-chloro-3-oxopentanoate (0.107 g, 0.650 mmol) in 1.5 mL of ethanol, O-(Trimethylsilyl)hydroxylamine (0.120 g, 0.975 mmol) and ammonium acetate (0.125 g, 1.625 mmol) were added and the resulting mixture was stirred at room temperature for 1 h. The crude was transferred into a microwave vial then 0.052 g (0.650 mmol) of 3-fluorobenzenecarbothioamide were added. The vial was sealed and irradiated at 120° C. for 50 minutes. The solution was cooled at room temperature and the solvent removed by vacuum distillation. The crude was purified by flash chromatography (dichloromethane:methanol 99:1 as eluent) to obtain 2-(3-fluorophenyl)-5-propanimidoyl-1,3-thiazol-4-ol as a yellow solid (0.078 mg, 0.31 mmol, Y=48%).

$^1$H-NMR (CDCl$_3$): δ 10.50 (bs, 1H, OH), 7.87-7.79 (m, 2H), 7.51-7.43 (m, 1H), 7.26-7.20 (m, 1H), 2.60 (q, 2H, J=7.3 Hz), 1.42 (t, 3H, J=7.3 Hz).

MS (ES$^{1+}$) m/z: 251.34 [M+H]$^+$.

Example 44

Synthesis of 2-(3-fluorophenyl)-5-[(1E)-N-hydroxypropanimidoyl]-1,3-thiazol-4-ol (44)

A solution of 0.040 g (0.143 mmol) of 2-(3-fluorophenyl)-5-[(1E)-N-methoxypropanimidoyl]-1,3-thiazol-4-ol (example 42) in dry dichloromethane (5 mL) was then refrigerated to 0° C. with an ice bath. The solution was treated at this temperature with boron tribromide 1M in dichloromethane (0.36 mL, 0.36 mmol) then stirred for 30 minutes. The reaction was diluted with DCM (5 mL) and stirred with water (5 mL) for 10 minutes. The organic layer was separated and anhydrified over anhydrous sodium sulphate, the solvent was distilled and the crude purified over silica gel.

2-(3-fluorophenyl)-5-[(1E)-N-hydroxypropanimidoyl]-1,3-thiazol-4-ol was obtained as a orange solid (0.031 g, 0.118 mmol, Y=83%).

$^1$H-NMR (CD$_3$OD): δ 7.81-7.78 (m, 1H), 7.77-7.73 (m, 1H), 7.50-7.22 (m, 2H), 2.81 (q, 2H, J=7.3 Hz), 1.54 (t, 3H, J=7.3 Hz).

MS (ES$^{1+}$) m/z: 267.22 [M+H]$^+$.

Example 45

Synthesis of cyclopropyl[2-(3-fluorophenyl)-4-hydroxy-1,3-thiazol-5-yl]methanone (45)

Starting from 3-fluorobenzenecarbothioamide (0.085 g, 0.55 mmol) prepared as described in Example 1—intermediate a, the general procedure for the thiazoles synthesis was applied to obtain 2-(3-fluorophenyl)-N,4-dimethoxy-N-methyl-1,3-thiazole-5-carboxamide (Weinreb's amide). The latter was subjected to the same synthetic conditions specified in the general procedure using cyclopropylmagnesium bromide to obtain cyclopropyl[2-(3*/ -fluorophenyl)-4-methoxy-1,3-thiazol-5-yl]methanone which was then deprotected with boron tribromide to obtain the title compound as a light brown solid (0.121 g, 0.46 mmol, Y=81%).

$^1$H-NMR (CDCl$_3$): δ 11.50 (bs, 1H, OH), 7.83-7.78 (m, 2H), 7.53-7.41 (m, 1H), 7.29-7.21 (m, 1H), 2.38 (m, 1H), 0.95-0.88 (m, 2H), 0.63-0.55 (m, 2H).

MS (ES$^{1+}$) m/z: 264.40 [M+H]$^+$.

Example 46

Evaluation of In Vitro Activity a. Cloning, Sequencing, Transfection and Selection of Positive Clones Expressing Human TRPM8

A functional cell-based assay for the identification of TRPM8 receptor antagonists, optimised to allow high throughput screening at FLIPR$^{TETRA}$, was developed in HEK293 cells by stable pure clone selection and functional characterization with a fluorescent calcium sensitive dye.

TRPM8 was cloned into the multiple cloning site of pcDNA3 mammalian expression vector; the obtained construct pcDNA3/hTRPM8 was fully sequence verified and used for the transfection of HEK293 cell line. HEK293 cells stably transfected with TRPM8 gene were maintained in Minimum essential medium. The cells were transfected with the pcDNA3/hTRPM8 vector by electroporation and then selected with medium containing 0.8 mg/ml G418 for 10-15 days.

The following commercial compounds were used as TRPM8 channel reference compound to test HEK293/hTRPM8 cell line for both agonist and antagonist activity:

Activators: Menthol (SIGMA cat. #M2772) WS-3, (N-Ethyl-5-methyl-2-(1-methylethyl) cyclohexanecarboxamide) (SIGMA cat. #W345501)

Blocker: Capsazepine (SIGMA cat. #C191)

The experimental activities were performed using FLIPR instruments.

The functional clones were selected at FLIPR$^{384}$ on the basis of 1 mM menthol response. Two best responder clones were selected, diluted at a cell density of 1 cell/well and analysed at FLIPR$^{384}$ with 1 mM menthol.

The TRPM8 receptor was analysed for the response to reference agonist, menthol, using a calcium-dependent fluorescence signal.

Patch clamp recordings were also obtained in voltage-clamp configuration on HEK/TRPM8 clones in order to verify the receptor pharmacology and to determine the agonist dose-response curve and EC$_{50}$ value. HEK293 cells were maintained at room temperature on an fire-polished borosilicate glass pipettes having 1.5-2.5 MΩ resistance were used to record currents following drug application. Menthol application induced a dose-dependent inward current in a selected HEK/hTRPM8 clone (calculated EC$_{50}$ value=58 μM). No menthol-induced currents were recorded in not transfected HEK293 cells.

In order to determine the capsazepine antagonist activity on menthol agonist response and to verify the antagonist response stability throughout different days of experiments, the selected clone of TRPM8 was analysed after 24 h at FLIPR$^{384}$ in presence of variable concentrations of antagonist (from 100 nM to 316 μM). The selected clone showed very good stability and reproducibility of the antagonist activity (calculated IC$_{50}$ value=20 μM).

Summarizing, the best clone was characterized for:
1—pharmacology: agonist EC$_{50}$ and antagonist IC$_{50}$ determination over different experiments;
2—optimal cell density and seeding time;
3—DMSO sensitivity;
4—ligand stability;
5—patch clamp analysis.

b. Screening Set Up for the Identification of TRPM8 Antagonists

The following commercial compounds were used as ligands:

Activator: Cooling Agent 10 (Takasago CAS N. 87061-04-9)

Blocker: Capsazepine (SIGMA cat #D_5879)

The experimental activities were performed using FLIPR$^{TETRA}$ instruments.

HEK293 cells stably transfected with TRPM8 gene were maintained in Minimum essential medium.

The TRPM8 cell line was analysed for the response to a library of compounds using a Ca$^{2+}$ mobilization-dependent fluorescence signal in 384 wells microtiter plate format. The analysis was performed using the FLIPR$^{TETRA}$ (MDC) with the ICCD Camera.

The execution of the assay involved the use of three microtiter plates:

1. Assay plate, containing cells loaded with dye and prepared as follows:

Cells were seeded at 15000 c/well in Poly-D-Lysine coated 384 wells Microtiter Plates in complete medium (25 μl/well).

24 h after seeding, the cell plates were washed with Tyrode assay buffer by the Microplate Washer and 10 μL of Tyrode assay buffer was left in each well.

Cells were then loaded with 10 μL/well of the Fluo-4 NW dye solution by CyBi®-Well pipettor. Each bottle of Fluo4-NW dye (Molecular Probes cat. #F36206, component A) was re-suspended in 8 mL of Tyrode assay buffer and supplemented with 100 μL of water-soluble probenecid (MolecularProbes cat. #F36206, component B).

Dye loaded cell plates were incubated for 1 h at room temperature.

2. Compound Dilution Plate, containing diluted test compounds, formulated as follows:

Column 1: wells containing Assay Buffer plus DMSO 0.5% final

Column 2: wells alternating Max Signal Control in first injection (Maximum Response: Cooling Agent 10 at EC$_{100}$, 100 μM) and Min Signal Control in first injection (Assay buffer plus 0.5% DMSO final);

Columns 3-22: wells containing Assay Buffer plus 0.5% DMSO final. To these wells the compounds to be tested were added at 3× concentration.

Column 23: alternating wells of Max Signal Control in second injection (Assay buffer) and Min Signal Control in second injection (Antagonist Capsazepine $IC_{100}$, 50 μM) in Assay buffer plus 0.5% DMSO final;

Column 24: wells containing Capsazepine (Antagonist) at 8 concentrations in duplicate at final concentrations of 50 μM, 25 μM, 6.25 μM, 3.15 μM, 1.56 μM, 780 nM, 309 nM in Assay buffer plus 0.5% DMSO final.

3. Activator Plate, containing agonist Cooling Agent 10 at $EC_{80}$, formulated as follows:

Column 1: Cooling Agent 10 (Agonist) at 8 concentrations dose response in duplicate at final concentrations of 100 μM, 31.6 μM, 10 μM, 3.16 μM, 1 μM, 316 nM, 100 nM, 31.6 nM in Assay buffer;

Columns 2-24: Cooling Agent 10 (Agonist) at $EC_{80}$ (3 fold concentrated, 20 μM final) in Assay buffer.

The test was carried out according to a procedure comprising the following steps:

1. The samples contained in the wells of the Compound Plate were added to the corresponding wells of the Assay Plate by the FLIPR$^{TETRA}$, thus resulting in the addition in Columns 3-22 of the test compounds at 3× concentration to the cells of the assay plates. No mixing was performed in the assay wells and the signal of the emitted fluorescence was recorded for 300 seconds.

2. The samples contained in the wells of the Activator Plate were added to the corresponding wells of the Assay Plate by the FLIPR$^{TETRA}$, thus resulting in the addition in Columns 3-22 of the Assay Plate of the agonist compound in addition to the test compounds. The signal of the emitted fluorescence was recorded for 180 seconds.

Columns 1, 2, 23 and 24 were used as control. In particular: the "Max Signal Control in first injection" indicates the Cooling Agent 10 agonist response at $EC_{100}$, "Max Signal Control in the second injection" indicates the agonist at $EC_{80}$ (10 μM) in presence of pre-injected Assay buffer, the "Min Signal Control in first injection" corresponds to Assay buffer injection and "Min Signal Control in the second injection" indicates the agonist at $EC_{80}$ (20 μM) in presence of pre-injected reference antagonist Capazepine at $IC_{100}$ (50 μM).

During the Target Activation (TA) phase, the injection of the reference agonist at $EC_{80}$ gave an increase of fluorescent signal in MAX Signal control wells in which the assay buffer in CA was preinjected, while the response was completely inhibited in MIN Signal control wells due to the preinjection of the reference inhibitor Capsazepine.

The goal of the assay was to find antagonists of TRPM8 activity; to this aim the change of fluorescent signal during TA phase was measured.

Several parameters were computed and analyzed (Z' factor, Interplate variability, Intraplate variability, Day to Day variability, Antagonist Dose response and $IC_{50}$ determination, Agonist Dose response and $EC_{50}$ determination).

As for the antagonist Dose response and $IC_{50}$ determination, capsazepine (reference antagonist) was included as control and the $IC_{50}$ values of all the assayed compounds were calculated.

Compounds 1-45 were tested and all showed an $IC_{50}$ value below 2 μM; the majority of the compounds having a $IC_{50}$ below 0.1 μM, some of them having a $IC_{50}$ below 0.03 μM.

Example 47

Evaluation of In Vivo Activity
Chronic Constriction Model of Pain

Neuropathic pain behavior will be induced by ligation of the sciatic nerve according to the method described by Bennett G J et al., Pain. 33: 87-107, 1988. Briefly, male Sprague-Dawley rats will be anaesthetized (100 mg/kg ketamine and 10 mg/kg xylazine i.p.) and the left sciatic nerve will be exposed at the level of the thigh by blunt dissection through the biceps femoris. Proximal to the sciatic's trifurcation, about 12 mm of nerve will be freed of adhering tissue and four ligatures will be loosely tied around it with about 1 mm spacing so that the epineural circulation will be preserved. The length of nerve thus affected was 6-8 mm long. The animals will be allowed to recover and used the day after the surgery. Sham animals represent rats operated but not ligated.

The study was performed in order to determine antiallodynic effects of compound 2. On day 7 and 14 following ligation, neuropathic rats was received a single dose of compound 2; 1, 3 and 5 h following treatment, mechanical and cold allodynia were evaluated using Dynamic Plantar Aesthesiometer (DPA) and drop of acetone.

All data were presented as the mean±SEM. Analysis of data was conducted using GraphPad Prism 4.01. Statistical analysis was performed by two-way ANOVA followed by Dunnett's test for multiple comparisons, as appropriate. Statistical significance was set at $p<0.05$.

Oral administration of compound 2 at the dose of 10 mg/kg on day 7 and on day 14 after nerve-induced injury, significantly attenuated cold and mechanical allodynia at 3 hours and 5 hours post-dose. The maximal activity was reached at 3 hours after treatment (about 50% of inhibition on both the parameters, FIGS. 1a, 1b, 2a and 2b) according to its pharmacokinetic profile.

Example 48

Selectivity Analysis
a. GPCRs Selectivity

Compound 2 was tested to evaluate the activity towards cloned human GPCRs (G-protein coupled receptors) using radioligand binding assays The compound was tested at 10 μM in duplicate and the results are summarized in Table 1.

TABLE 1

| Receptor | Cmpd 2 |
| --- | --- |
| human Muscarinic $M_2$ | inactive |
| human Muscarinic $M_3$ | inactive |
| human Adrenergic $\beta_1$ | inactive |
| human Adrenergic $\beta_2$ | inactive |
| human Adrenergic $\alpha_{1A}$ | inactive |
| human Adrenergic $\alpha_{2A}$ | inactive |
| human Serotoninergic 5-$HT_{1A}$ | inactive |
| human Histamine $H_1$ | inactive |
| human Histamine $H_2$ | inactive |
| human Cannabinoid $CB_1$ | inactive |
| human Cannabinoid $CB_2$ | inactive |
| human Bradykinin $B_1$ | inactive |
| human Bradykinin $B_2$ | inactive |
| human Dopamine $D_{2S}$ | inactive |
| human Dopamine $D_3$ | inactive |
| human Opioid δ2 (DOP) | inactive |
| human Opioid κ (KOP) | inactive |
| human Opioid μ (MOP) | inactive |
| human Opioid NOP (ORL1) | inactive |
| human NK1 | inactive |

As it is possible to note from Table 1, compound 2 shows a high selectivity versus a wide range of selected GPCRs (including muscarinic M3, CB2, BK1, alpha e beta adrenergic) that are well know to be involved in the pain control. These data support that the observed in vivo efficacy of compound 2 and in general of all the compounds of the invention is potential strongly dependent on the TRPM8 blockage.

b. Ion Channel Selectivity.

In order to address more specifically the potential selectivity issues, a counterassay was carried out for compound 2 against TRPV1 and TRPV4 ion channels, both involved in the nociception (Jhaveri M D, et al 2005. Eur. J. Neurosci. 22 (2): 361-70, Brierley S M et al, 2008, Gastroenterology. 2008 June; 134(7):2059-69) and towards TRPA1. The results are summarized in Table 2.

The ability of compound 2 to act as an antagonist of TRPV1 was evaluated with a calcium influx assay. The signal elicited in the presence of the positive control agonist (capsaicin) was set to 100% and the signal in the presence of the antagonist (ruthenium red) was set to 0. In parallel, the ability of compound 2 to act as an antagonist of TRPV4 was evaluated with a calcium influx assay. The signal elicited in the presence of the positive control agonist (GSK1016790A) was set to 100% and the signal in the presence of the antagonist (ruthenium red) was set to 0. The ability of compound 2 to act as an antagonist of TRPA1 was evaluated with a calcium influx assay. The signal elicited in the presence of the positive control agonist (allyl isothiocyanate, AITC) was set to 100% and the signal in the presence of the antagonist (ruthenium red) was set to 0.

TABLE 2

| Compound | $IC_{50}$ (TRPV1) | $IC_{50}$ (TRPV4) | $IC_{50}$ (TRPA1) |
|---|---|---|---|
| 2 | $>10^5$ M | $>10^5$ M | $>10^5$ M |

The data strongly highlight the great selectivity of compound 2 towards TRPV1, TRPV4 and TRPA1 thus confirming its selective mechanism of action.

Example 49

ADME and PK Evaluation

The ADME properties and the pharmacokinetic profile of compound 2 were evaluated. The results are summarized in Table 3 and Table 4:

TABLE 3

| | |
|---|---|
| Log $D_{7.4}$ | 0.440 |
| pKa | 4.18 |
| hERG (IC50) | >1 mM |
| CYP450 Inhibition (IC50 at 10 μM) | CYP3A4, CYP1A2, CYP2D6, CYP2C9, CYP2C19 > 30 μM |
| Plasma Protein Binding | human 98.71%-rat 97.50% |
| $CL_{int}$ (rat) | 29.4 μL/min/mg |
| Rat Plasma Stability (% remaining) | 98.2% at 30 min, 80.3 at 60 min |

TABLE 4

| Compound | intravenous administration | | | oral administration | | | | | |
|---|---|---|---|---|---|---|---|---|---|
| | CL (mL/min/kg) | Vds (L/kg) | $t_{1/2}$ (h) | Cmax (ng/mL) | AUC (ng · h/mL) | $t_{max}$ (h) | CL (mL/min/kg) | $t_{1/2}$ (h) | F (%) |
| 2[a] | 6.81 | 1.78 | 3.01 | 10295 | 26134 | 0.25 | 6.41 | 2.94 | 100 |

[a]IV 5 mg/kg; PO 10 mg/kg

Compound 2 shows no effect towards any human cytochrome isoform at the maximal concentration of 10 uM thus excluding potential drug drug interaction. In addition, none effect was observed towards hERG channel thus excluding potential cardiotoxic effect during the clinical development.

The low log D values of compound 2 makes it particularly suitable when ip, iv and i ves applications are required, especially in the treatment of urological disorders. At the same time, the relatively high plasma half-life (2.94 h) and the high oral bioavailability (F=100%) could makes it the ideal candidate for the treatment of chronic diseases, like inflammatory and neuropathic pain.

TABLE 5

| Compound Number | Structure | Chemical Name | IC50 (μM) |
|---|---|---|---|
| 1 | (structure) | 1-[2-(3-fluorophenyl)-4-hydroxy-1,3-thiazol-5-yl]propan-1-one | 0.032 |

TABLE 5-continued

| Compound Number | Structure | Chemical Name | IC50 (μM) |
|---|---|---|---|
| 2 | 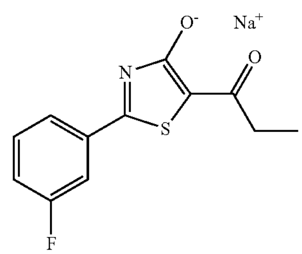 [SMILES: CCC(=O)c1sc(-c2cccc(F)c2)nc1[O-] ; [Na+]] | Sodium 2-(3-fluorophenyl)-5-propanoyl-1,3-thiazol-4-olate | 0.028 |
| 3 | 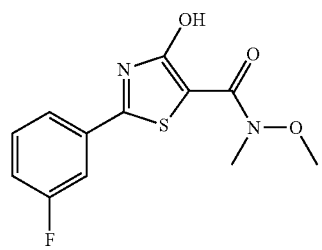 [SMILES: CON(C)C(=O)c1sc(-c2cccc(F)c2)nc1O] | 2-(3-fluorophenyl)-4-hydroxy-N-methoxy-N-methyl-1,3-thiazole-5-carboxamide | 0.018 |
| 4 | 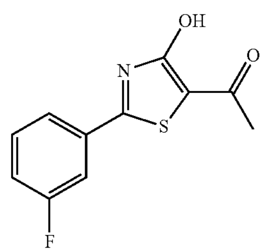 [SMILES: CC(=O)c1sc(-c2cccc(F)c2)nc1O] | 1-(2-(3-fluorophenyl)-4-hydroxythiazol-5-yl)ethanone | 0.958 |
| 5 | 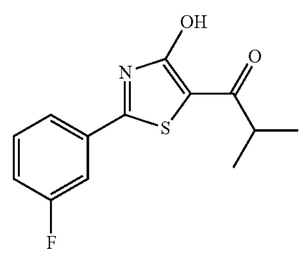 [SMILES: CC(C)C(=O)c1sc(-c2cccc(F)c2)nc1O] | 1-[2-(3-fluorophenyl)-4-hydroxy-1,3-thiazol-5-yl]-2-methylpropan-1-one | 0.299 |
| 6 | 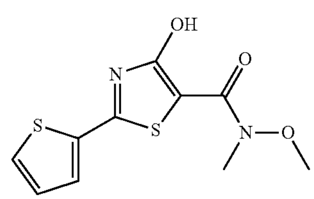 [SMILES: CON(C)C(=O)c1sc(-c2cccs2)nc1O] | 4-hydroxy-N-methoxy-N-methyl-2-(thiophen-2-yl)-1,3-thiazole-5-carboxamide | 0.156 |
| 7 | 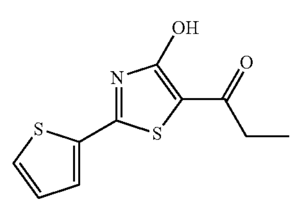 | 1-[4-hydroxy-2-(thiophen-2-yl)-1,3-thiazol-5-yl]propan-1-one | 0.596 |

TABLE 5-continued

| Compound Number | Structure | Chemical Name | IC50 (μM) |
|---|---|---|---|
| 8 | 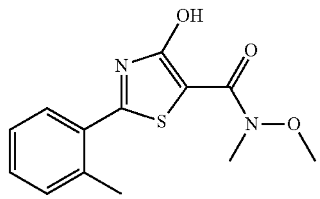 [SMILES: CON(C)C(=O)c1sc(-c2ccccc2C)nc1O] | 4-hydroxy-N-methoxy-N-methyl-2-(2-methylphenyl)-1,3-thiazole-5-carboxamide | 0.086 |
| 9 | 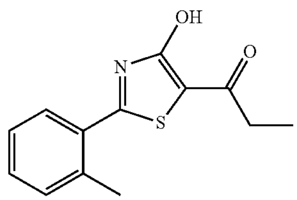 [SMILES: CCC(=O)c1sc(-c2ccccc2C)nc1O] | 1-[4-hydroxy-2-(2-methylphenyl)-1,3-thiazol-5-yl]propan-1-one | 0.411 |
| 10 | 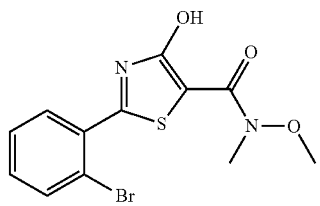 [SMILES: CON(C)C(=O)c1sc(-c2ccccc2Br)nc1O] | 2-(2-bromophenyl)-4-hydroxy-N-methoxy-N-methyl-1,3-thiazole-5-carboxamide | 0.435 |
| 11 | 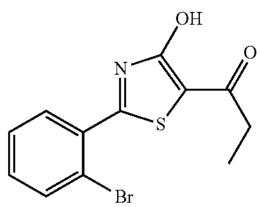 [SMILES: CCC(=O)c1sc(-c2ccccc2Br)nc1O] | 1-[2-(2-bromophenyl)-4-hydroxy-1,3-thiazol-5-yl]propan-1-one | 0.912 |
| 12 | 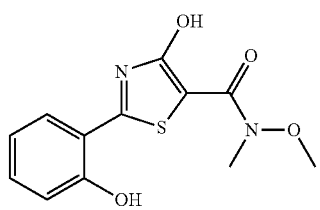 [SMILES: CON(C)C(=O)c1sc(-c2ccccc2O)nc1O] | 4-hydroxy-2-(2-hydroxyphenyl)-N-methoxy-N-methyl-1,3-thiazole-5-carboxamide | 0.006 |
| 13 | 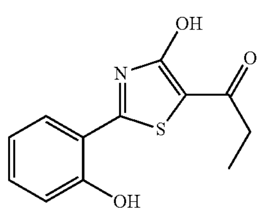 [SMILES: CCC(=O)c1sc(-c2ccccc2O)nc1O] | 1-[2-(2-hydroxyphenyl)-4-hydroxy-1,3-thiazol-5-yl]propan-1-one | 0.112 |
| 14 | 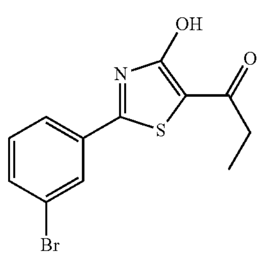 [SMILES: CCC(=O)c1sc(-c2cccc(Br)c2)nc1O] | 1-[2-(3-bromophenyl)-4-hydroxy-1,3-thiazol-5-yl]propan-1-one | 1.73 |

TABLE 5-continued

| Compound Number | Structure | Chemical Name | IC50 (μM) |
|---|---|---|---|
| 15 | 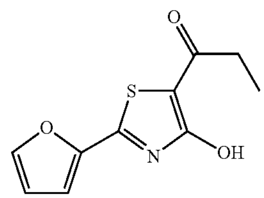 | 1-[2-(furan-2-yl)-4-hydroxy-1,3-thiazol-5-yl]propan-1-one | 0.236 |
| 16 | 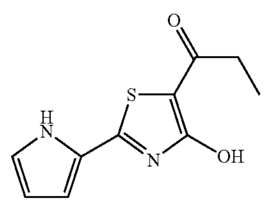 | 1-[4-hydroxy-2-(1H-pyrrol-2-yl)-1,3-thiazol-5-yl]propan-1-one | 0.123 |
| 17 | 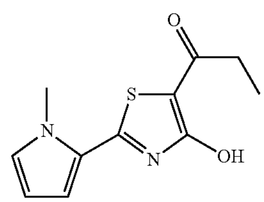 [SMILES: CCC(=O)c1sc(-c2cccn2C)nc1O] | 1-[4-hydroxy-2-(1-methyl-1H-pyrrol-2-yl)-1,3-thiazol-5-yl]propan-1-one | 0.323 |
| 18 | 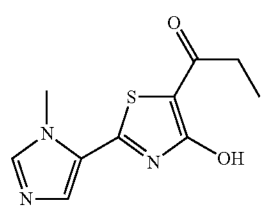 [SMILES: CCC(=O)c1sc(-c2cncn2C)nc1O] | 1-[4-hydroxy-2-(1-methyl-1H-imidazol-5-yl)-1,3-thiazol-5-yl]propan-1-one | 0.112 |
| 19 | 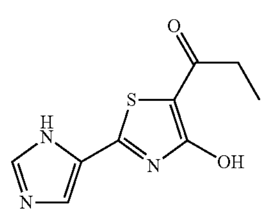 | 1-[4-hydroxy-2-(1H-imidazol-5-yl)-1,3-thiazol-5-yl]propan-1-one | 0.302 |
| 20 | 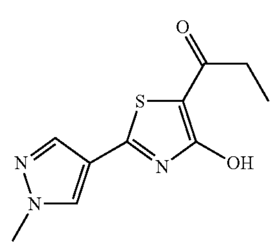 [SMILES: CCC(=O)c1sc(-c2cnn(C)c2)nc1O] | 1-[4-hydroxy-2-(1-methyl-1H-pyrazol-4-yl)-1,3-thiazol-5-yl]propan-1-one | 0.089 |
| 21 | 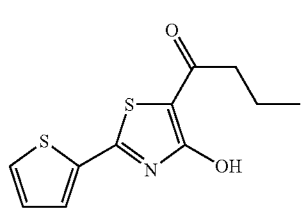 [SMILES: CCCC(=O)c1sc(-c2cccs2)nc1O] | 1-[4-hydroxy-2-(thiophen-2-yl)-1,3-thiazol-5-yl]butan-1-one | 0.064 |

TABLE 5-continued

| Compound Number | Structure | Chemical Name | IC50 (μM) |
|---|---|---|---|
| 22 | 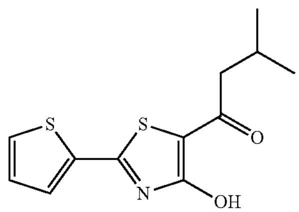 [SMILES: CC(C)CC(=O)c1sc(-c2cccs2)nc1O] | 1-[4-hydroxy-2-(thiophen-2-yl)-1,3-thiazol-5-yl]-3-methylbutan-1-one | 0.085 |
| 23 | 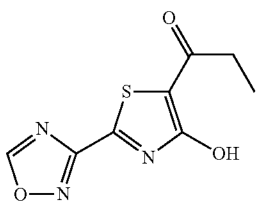 | 1-[4-hydroxy-2-(1,2,4-oxadiazol-3-yl)-1,3-thiazol-5-yl]propan-1-one | 0.099 |
| 24 | 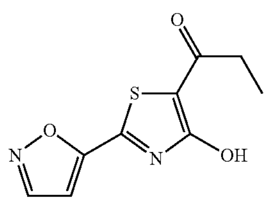 | 1-[4-hydroxy-2-(1,2-oxazol-5-yl)-1,3-thiazol-5-yl]propan-1-one | 0.123 |
| 25 | 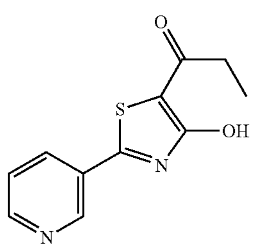 [SMILES: CCC(=O)c1sc(-c2cccnc2)nc1O] | 1-[4-hydroxy-2-(pyridin-3-yl)-1,3-thiazol-5-yl]propan-1-one | 0.356 |
| 26 | 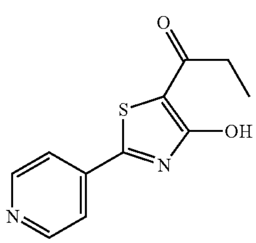 [SMILES: CCC(=O)c1sc(-c2ccncc2)nc1O] | 1-[4-hydroxy-2-(pyridin-4-yl)-1,3-thiazol-5-yl]propan-1-one | 0.453 |
| 27 | 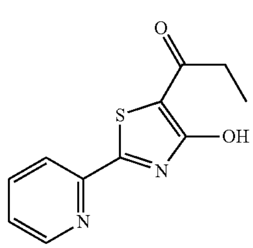 [SMILES: CCC(=O)c1sc(-c2ccccn2)nc1O] | 1-[4-hydroxy-2-(pyridin-2-yl)-1,3-thiazol-5-yl]propan-1-one | 0.145 |

TABLE 5-continued

| Compound Number | Structure | Chemical Name | IC50 (μM) |
|---|---|---|---|
| 28 | 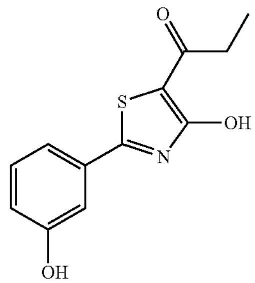 [SMILES: CCC(=O)c1sc(-c2cccc(O)c2)nc1O] | 1-[4-hydroxy-2-(3-hydroxyphenyl)-1,3-thiazol-5-yl]propan-1-one | 0.023 |
| 29 | 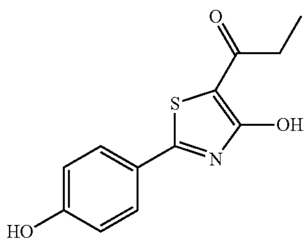 [SMILES: CCC(=O)c1sc(-c2ccc(O)cc2)nc1O] | 1-[4-hydroxy-2-(4-hydroxyphenyl)-1,3-thiazol-5-yl]propan-1-one | 0.326 |
| 30 | 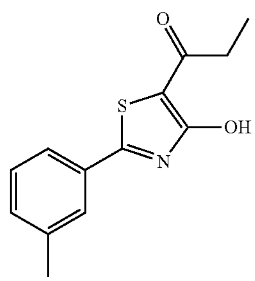 [SMILES: CCC(=O)c1sc(-c2cccc(C)c2)nc1O] | 1-[4-hydroxy-2-(3-methylphenyl)-1,3-thiazol-5-yl]propan-1-one | 0.231 |
| 31 | 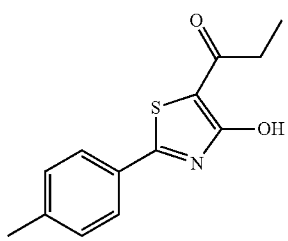 [SMILES: CCC(=O)c1sc(-c2ccc(C)cc2)nc1O] | 1-[4-hydroxy-2-(4-methylphenyl)-1,3-thiazol-5-yl]propan-1-one | 0.236 |
| 32 | 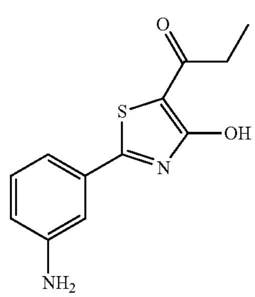 [SMILES: CCC(=O)c1sc(-c2cccc(N)c2)nc1O] | 1-[2-(3-aminophenyl)-4-hydroxy-1,3-thiazol-5-yl]propan-1-one | 0.450 |
| 33 | 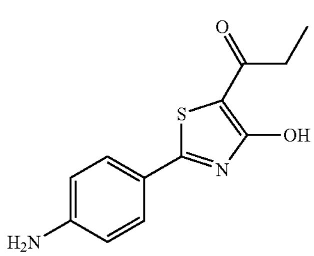 [SMILES: CCC(=O)c1sc(-c2ccc(N)cc2)nc1O] | 1-[2-(4-aminophenyl)-4-hydroxy-1,3-thiazol-5-yl]propan-1-one | 0.632 |

TABLE 5-continued

| Compound Number | Structure | Chemical Name | IC50 (μM) |
|---|---|---|---|
| 34 | 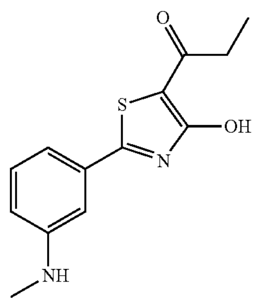 [SMILES: CCC(=O)c1sc(-c2cccc(NC)c2)nc1O] | 1-{4-hydroxy-2-[3-(methylamino)phenyl]-1,3-thiazol-5-yl}propan-1-one | 0.233 |
| 35 | 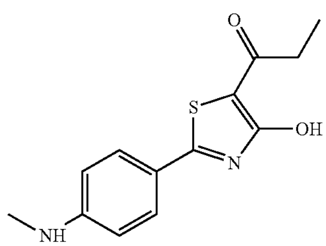 [SMILES: CCC(=O)c1sc(-c2ccc(NC)cc2)nc1O] | 1-{4-hydroxy-2-[4-(methylamino)phenyl]-1,3-thiazol-5-yl}propan-1-one | 0.789 |
| 36 | 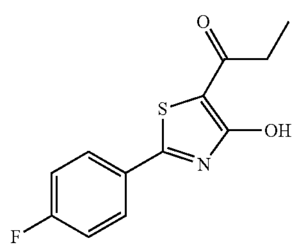 [SMILES: CCC(=O)c1sc(-c2ccc(F)cc2)nc1O] | 1-[2-(4-fluorophenyl)-4-hydroxy-1,3-thiazol-5-yl]propan-1-one | 0.050 |
| 37 | 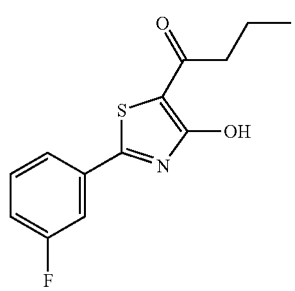 [SMILES: CCCC(=O)c1sc(-c2cccc(F)c2)nc1O] | 1-(2-(3-fluorophenyl)-4-hydroxythiazol-5-yl)butan-1-one | 0.142 |
| 38 | 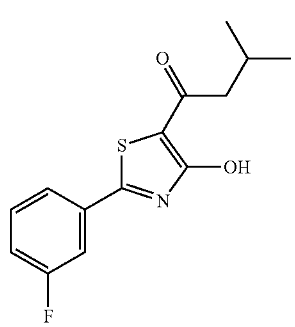 [SMILES: CC(C)CC(=O)c1sc(-c2cccc(F)c2)nc1O] | 1-(2-(3-fluorophenyl)-4-hydroxythiazol-5-yl)isobutan-1-one | 0.331 |

TABLE 5-continued

| Compound Number | Structure | Chemical Name | IC50 (μM) |
|---|---|---|---|
| 39 | 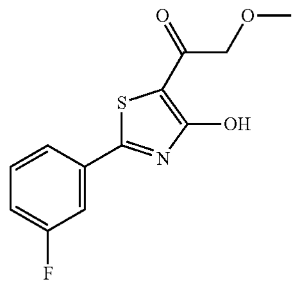 [SMILES: COCC(=O)c1sc(-c2cccc(F)c2)nc1O] | 1-[2-(3-fluorophenyl)-4-hydroxy-1,3-thiazol-5-yl]-2-methoxyethanone | 0.523 |
| 40 | 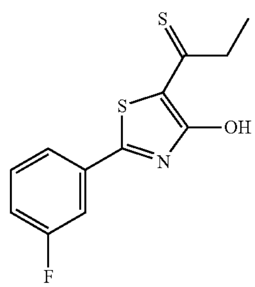 [SMILES: CCC(=S)c1sc(-c2cccc(F)c2)nc1O] | 1-[2-(3-fluorophenyl)-4-hydroxy-1,3-thiazol-5-yl]propane-1-thione | 0.236 |
| 41 | 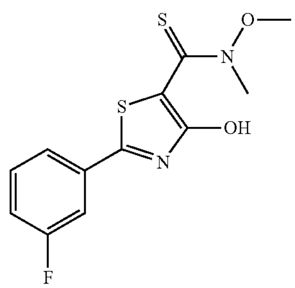 [SMILES: CON(C)C(=S)c1sc(-c2cccc(F)c2)nc1O] | 2-(3-fluorophenyl)-4-hydroxy-N-methoxy-N-methyl-1,3-thiazole-5-carbothioamide | 0.388 |
| 42 | 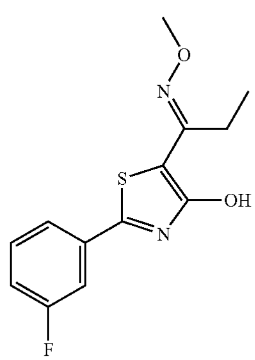 [SMILES: CC/C(=N\OC)c1sc(-c2cccc(F)c2)nc1O] | 2-(3-fluorophenyl)-5-[(1E)-N-methoxypropanimidoyl]-1,3-thiazol-4-ol | 0.986 |
| 43 | 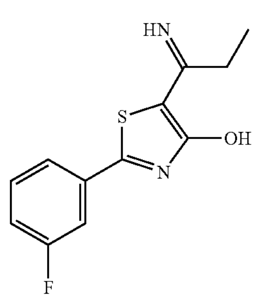 [SMILES: CCC(=N)c1sc(-c2cccc(F)c2)nc1O] | 2-(3-fluorophenyl)-5-propanimidoyl-1,3-thiazol-4-ol | 1.21 |

TABLE 5-continued

| Compound Number | Structure | Chemical Name | IC50 (μM) |
|---|---|---|---|
| 44 | 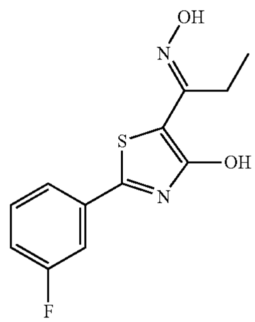 [SMILES: CC/C(=N\O)c1sc(-c2cccc(F)c2)nc1O] | 2-(3-fluorophenyl)-5-[(1E)-N-hydroxypropanimidoyl]-1,3-thiazol-4-ol | 1.36 |
| 45 | 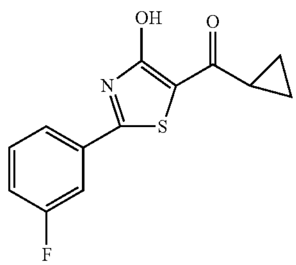 [SMILES: O=C(c1sc(-c2cccc(F)c2)nc1O)C1CC1] | cyclopropyl[2-(3-fluorophenyl)-4-hydroxy-1,3-thiazol-5-yl]methanone | 0.287 |

The invention claimed is:

1. A compound selected from the group consisting of:
    sodium 2-(3-fluorophenyl)-5-propanoyl-1,3-thiazol-4-olate,
    2-(3-fluorophenyl)-4-hydroxy-N-methoxy-N-methyl-1,3-thiazole-5-carboxamide,
    4-hydroxy-2-(2-hydroxyphenyl)-N-methoxy-N-methyl-1,3-thiazole-5- carboxamide and
    1-[4-hydroxy-2-(3-hydroxyphenyl)-1,3-thiazol-5-yl]propan-1-one.

2. A pharmaceutical composition comprising as the active ingredient at least one compound according to claim 1 in combination with pharmaceutically acceptable excipients and/or diluents.

3. A method of treating a disease associated with overexpression and/or hyperactivity of the Transient Receptor Potential cation channel subfamily M member 8 (TRPM8) in a subject in need thereof, comprising administration of an effective amount of a compound of formula (I) to the subject:

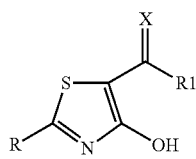

(I)

wherein
X is oxygen, sulphur, NH, NOH, or NOMe;
R is a group selected from aryl and heteroaryl, optionally substituted by one or more substituents selected from the group consisting of:
    hydrogen,
    halogen,
    $CF_3$,
    linear or branched $C_1$-$C_6$ alkyl,
    OR5 and
    NR6R7, wherein R5, R6 and R7 are independently hydrogen or linear or branched $C_1$-$C_6$ alkyl; and
R1 is a group selected from the group consisting of:
    linear or branched $C_1$-$C_6$ alkyl,
    $(CH_2)_m$-OR2, wherein m is an integer between 1 and 3 and R2 is selected from hydrogen and linear $C_1$-$C_3$ alkyl,
    $C_3$-$C_6$ cycloalkyl, and
    N(R3)OR4, wherein R3 and R4 are independently hydrogen or linear or branched $C_1$-$C_3$ alkyl,
or a pharmaceutically acceptable salt thereof.

4. The method according to claim 3, wherein X is oxygen.

5. The method according to claim 3, wherein
    R is phenyl or a 5- or 6-membered heteroaryl having from 1 to 3 heteroatoms selected from the group consisting of N, O and S.

6. The method according to claim 5, wherein R is selected from the group consisting of thiophenyl, furanyl, pyrrolyl, imidazolyl, pyrazolyl, oxadiazolyl, oxazolyl and pyridinyl.

7. The method according to claim 3, wherein
    R is aryl optionally substituted with a group selected from the group consisting of:
    halogen,
    linear or branched $C_1$-$C_3$ alkyl,
    OR5 and NR6R7, wherein R5, R6 and R7 are independently hydrogen or linear or branched $C_1$-$C_3$ alkyl.

8. The method according to claim 7, wherein
    R is aryl optionally substituted with a group selected from the group consisting of:
    Br, F,
    $CH_3$,
    OH, —$NH_2$, and $NHCH_3$.

9. The method according to claim 3, wherein
    R is heteroaryl and the heteroaryl is optionally substituted with linear or branched $C_1$-$C_6$ alkyl.

10. The method according to claim 9, wherein R is heteroaryl optionally substituted with methyl.

11. The method according to claim 3, wherein
R is selected from the group consisting of 3-fluorophenyl, 4-fluorophenyl, 2-bromophenyl, 3-bromophenyl, 2-methylphenyl, 3-methylphenyl, 4-methylphenyl, 2-hydroxyphenyl, 3-hydroxyphenyl, 4-hydroxyphenyl, 3-aminophenyl, 4-aminophenyl, 3-methylaminophenyl, 4-methylaminophenyl, thiophen-2yl, furan-2yl, pyrrol-2yl, 1H-imidazol-5yl, 1-methyl-imidazol-5yl, pyrazol-4yl, 1,2,4-oxadiazol-3yl, 1,2-oxazol-5yl, pyridin-2yl, pyridin-3yl and pyridin-4yl.

12. The method according to claim 3, wherein
R1 is
linear or branched $C_1$-$C_6$ alkyl,
$(CH2)_m$-OR2 wherein m is 1 and R2 is linear $C_1$-$C_3$ alkyl,
$C_3$-$C_6$ cycloalkyl, or
N(R3)OR4.

13. The method according to claim 3, wherein
R1 is
linear or branched $C_1$-$C_6$ alkyl,
$(CH2)_m$-OR2 wherein m is 1 and R2 is $CH_3$,
cyclopropyl,
or
N(R3)OR4, wherein R3 and R4 are independently $C_1$-$C_3$ alkyl.

14. The method according to claim 13, wherein R3 and R4 are $CH_3$.

15. The method according to claim 3, wherein
R1 is selected from the group consisting of:
methyl, ethyl, isopropyl, isobutyl, $CH_2OCH_3$, cyclopropyl and —$N(CH_3)OCH_3$.

16. The method according to claim 3, wherein the disease is selected from the group consisting of itch, irritable bowel diseases, cold-induced and/or exhacerbated respiratory disorders, ischemia, pain, urological disorders, stroke, psychiatric disorders and neurodegeneration.

17. The method according to claim 16, wherein the disease is selected from the group consisting of chronic pain, neuropathic pain, postoperative pain, cancer pain, osteoarthritic pain, rheumatoid arthritic pain, neuralgia, fibromyalgia, neuropathies, algesia, nerve injury, migraine, headache, itch, irritable bowel disease, painful bladder syndrome, interstitial cystitis, detrusor overactivity, urinary incontinence, benign prostatic hyperpiesia, lower urinary tract disorders and lower urinary tract symptoms, anxiety, depression and cold-induced/or exhacerbated pulmonary hypertension, chronic obstructive pulmonary disease (COPD) and asthma.

18. The method according to claim 17, wherein the disease is neurogenic detrusor overactivity or idiopathic detrusor overactivity.

* * * * *